US006876885B2

(12) United States Patent
Swoyer et al.

(10) Patent No.: US 6,876,885 B2
(45) Date of Patent: Apr. 5, 2005

(54) IMPLANTABLE BIFURCATED GASTROINTESTINAL LEAD WITH ACTIVE FIXATION

(75) Inventors: John M. Swoyer, Andover, MN (US); Warren Starkebaum, Plymouth, MN (US); Martin T. Gerber, Maple Grove, MN (US); Tim Herbert, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 424 days.

(21) Appl. No.: 10/046,011

(22) Filed: Jan. 11, 2002

(65) Prior Publication Data

US 2002/0103522 A1 Aug. 1, 2002

Related U.S. Application Data

(60) Provisional application No. 60/265,219, filed on Jan. 31, 2001, provisional application No. 60/265,369, filed on Jan. 31, 2001, and provisional application No. 60/265,505, filed on Jan. 31, 2001.

(51) Int. Cl.[7] ............................................... A61N 1/05
(52) U.S. Cl. ...................................................... 607/116
(58) Field of Search ............................. 607/40, 41, 116, 607/133; 600/29, 30

(56) References Cited

U.S. PATENT DOCUMENTS

| 3,333,045 | A | 7/1967 | Fisher et al. |
| 3,472,234 | A | 10/1969 | Tachick |
| 3,737,579 | A | 6/1973 | Bolduc |
| 3,866,615 | A | 2/1975 | Hewson |
| 4,000,745 | A | 1/1977 | Goldberg |
| 4,010,758 | A | 3/1977 | Rockland et al. |
| 4,177,818 | A | 12/1979 | De Pedro |
| 4,235,246 | A | 11/1980 | Weiss |
| 4,313,448 | A | 2/1982 | Stokes |
| 4,357,946 | A | 11/1982 | Dutcher et al. |
| 4,424,818 | A | 1/1984 | Doring et al. |
| 4,452,254 | A | 6/1984 | Goldberg et al. |
| 5,328,442 | A | 7/1994 | Levine |
| 5,423,872 | A | 6/1995 | Cigaina |
| 5,425,751 | A | 6/1995 | Baeten et al. ............... 607/28 |
| 5,489,294 | A | 2/1996 | McVenes et al. ........... 607/120 |
| 5,507,289 | A | 4/1996 | Essen-Moller |
| 5,690,691 | A | 11/1997 | Chen et al. |

(Continued)

FOREIGN PATENT DOCUMENTS

GB           1277107          6/1972

Primary Examiner—George Manuel
(74) Attorney, Agent, or Firm—Thomas F. Woods

(57) ABSTRACT

Bifurcated, active fixation, gastrointestinal leads adapted to be implanted within the body at a site of the GI tract to conduct electrical stimulation and electrical signals of the GI tract between the gastrointestinal stimulator and the site are disclosed. The GI tract lead has a lead body comprising a common lead body trunk extending from a lead body trunk proximal end to a junction with a first plurality of lead body legs that extend from the junction to a like first plurality of lead body leg distal ends. An electrode head is formed at each lead body leg distal end having a plate and supporting at least one stimulation/sense electrode and an active fixation mechanism, whereby a plurality of active fixation attachment mechanisms are supported by a like plurality of electrode heads. The plurality of electrode heads can be affixed by the fixation mechanism at a plurality of spaced apart locations of the GI tract. The plurality of electrode heads can be affixed spaced apart an optimal distance for efficacious sensing and/or stimulation accommodating the physiology and any defects or surgical interventions of the physiology or other therapeutic equipment or IMDs that restrict full access to the GI tract.

87 Claims, 8 Drawing Sheets

U.S. PATENT DOCUMENTS

| | | | |
|---|---|---|---|
| 5,716,392 A | 2/1998 | Bourgeois et al. | 607/132 |
| 5,837,006 A | 11/1998 | Ocel et al. | 607/127 |
| 5,861,014 A | 1/1999 | Familoni | 607/40 |
| 6,026,326 A | 2/2000 | Bardy | |
| 6,083,249 A * | 7/2000 | Familoni | 607/40 |
| 6,091,992 A * | 7/2000 | Bourgeois et al. | 607/40 |
| 6,104,965 A | 8/2000 | Lim et al. | |
| 6,216,039 B1 | 4/2001 | Bourgeois | |
| 6,243,607 B1 | 6/2001 | Mintchev et al. | |
| 6,327,503 B1 * | 12/2001 | Familoni | 607/40 |

* cited by examiner

IMPLANTABLE BIFURCATED GASTROINTESTINAL LEAD WITH ACTIVE FIXATION

RELATED APPLICATIONS

This application claims priority to provisional U.S. Application Ser. No. 60/265,219, filed Jan. 31, 2001, provisional U.S. Application Ser. No. 60/265,369, filed Jan. 31, 2001, and provisional U.S. Application Ser. No. 60/265,505, filed Jan. 31, 2001.

This disclosure is related to the following co-pending application entitled IMPLANTABLE GASTROINTESTINAL LEAD WITH ACTIVE FIXATION by Swoyer et al (application Ser. No. 10/045,701; filed Jan. 11, 2002), which is not admitted as prior art with respect to the present disclosure by its mention in this section.

FIELD OF THE INVENTION

The present invention pertains to gastrointestinal leads adapted to be implanted within the body at a site of the gastrointestinal tract (GI tract) to conduct electrical stimulation from an implantable or external electrical neurostimulator to the site and to conduct electrical signals of the GI tract from the site to the implantable or external electrical neurostimulator, and particularly to a lead having two or more electrode heads bearing two or more active fixation mechanisms that can be independently activated to affix electrodes at two or more respective sites of the GI tract wall.

BACKGROUND OF THE INVENTION

The GI tract comprises the esophagus, the stomach, the small intestine, the large intestine, the colon, and the anal sphincter and is generally described as having a tract axis. Like other organs of the body, most notably the heart, these organs naturally undergo regular rhythmic contractions. In particular these contractions take the form of peristaltic contractions and are essential for the movement of food through each of the respective organs. Like the heart, these contractions are the result of regular rhythmic electrical depolarizations of the underlying tissue. With regards to the small intestine and large intestine, normal electrical depolarizations ("slow waves") typically occur at a rate of approximately 15 and 1 beats per minute (bpm) respectively. Similarly, in the stomach, normal slow waves typically occur at a rate approximately 3 bpm. Not all of these depolarizations, however, normally result in a contraction of the organ. Rather contractions occur upon the occurrence of a normal electrical depolarizations followed by a series of high frequency spike activity.

In some individuals, however, either the regular rhythmic peristaltic contractions do not occur or the regular rhythmic electrical depolarizations do not occur or both do not occur. In each of these situations the movement of food may be seriously inhibited or even disabled. Such a condition is often called "gastroparesis" when it its occurs in the stomach. Gastroparesis is a chronic gastric motility disorder in which there is delayed gastric emptying of solids or liquids or both. Symptoms of gastroparesis may range from early satiety and nausea in mild cases to chronic vomiting, dehydration, and nutritional compromise in severe cases. Similar motility disorders occur in the other organs of the GI tract, although by different names.

Diagnosis of gastroparesis is based on demonstration of delayed gastric emptying of a radiolabeled solid meal in the absence of mechanical obstruction. Gastroparesis may occur for a number of reasons. Approximately one third of patients with gastroparesis, however, have no identifiable underlying cause (often called idiopathic gastroparesis). Management of gastroparesis involves four areas: (1) prokinetic drugs, (2) antiemetic drugs, (3) nutritional support, and (4) surgical therapy (in a very small subset of patients.) Gastroparesis is often a chronic, relapsing condition; 80% of patients require maintenance antiemetic and prokinetic therapy and 20% require long-term nutritional supplementation. Other maladies such as tachygastria or bradygastria can also hinder coordinated muscular motor activity of the GI tract, possibly resulting in either stasis or nausea or vomiting or a combination thereof.

The undesired effect of these conditions is a reduced ability or complete failure to efficiently propel intestinal contents down the digestive tract. This results in malassimilation of liquid or food by the absorbing mucosa of the intestinal tract. If this condition is not corrected, malnutrition or even starvation may occur. Moreover nausea or vomiting or both may also occur. Whereas some of these disease states can be corrected by medication or by simple surgery, in most cases treatment with drugs is not adequately effective, and surgery often has intolerable physiologic effects on the body.

For many years, sensing of the peristaltic electrical wave and gastrointestinal stimulation at various sites on or in the GI tract wall of the digestive system or nerves associated therewith have been conducted to diagnose and treat these various conditions. The history and breadth of such sensing and GI tract stimulation is set forth in commonly assigned U.S. Pat. Nos. 5,507,289, 6,026,326, 6,104,965, 6,216,039, and in further U.S. Pat. Nos. 5,690,691 and 6,243,607, for example.

Electrical stimuli are applied from the neurostimulator implantable pulse generator (IPG) through leads and electrodes affixed at sites in the body of the patient or the GI tract wall that permit the electrical stimulus to produce a local contraction of a desired portion of the GI tract. The sites of the GI tract wall comprise the outermost serosa or sub-serosally in the inner, circumferential and longitudinal (and oblique in the case of the stomach) smooth muscle layers referred to as the "muscularis externa". The smooth muscle is preferably comprised of innervated muscle tissue, and it is theorized that the smooth muscle is neurally electrically stimulated through the nerves associated with and innervating the muscle tissue in order to produce the contraction of the smooth muscle.

An implantable method and system for electrical stimulation of smooth muscle with intact local gastric nerves comprising a portion of the GI tract is disclosed in the '607 patent. The electrical stimulation of the smooth muscle effects local contractions at sites of a portion of the GI tract that are artificially propagated distally therethrough in order to facilitate or aid at least a partial emptying of such portion. This stimulation attempts to create a simulated system that reproduces the spatial and temporal organization of normal gastric electrical activity by creating and controlling local circumferential non-propagated contractions. In this simulated gastric pacing system, each local circumferential contraction is invoked by applying an electrical stimulus to the smooth muscle circumferentially about the portion of the GI tract in a plane substantially perpendicular to the longitudinal axis of the portion. The electrical stimulus is applied at a proximal location and at at least one distal location. The distal location is in axially spaced relationship relative to the proximal location. Further, the applied electrical stimulus is selected to be sufficient to stimulate the smooth muscle to produce the local circumferential contractions at the proximal and distal locations.

The Medtronic® Itrel III® Model 7425 IPG and pairs of the unipolar Model 4300 or Model 4301 or Model 4351 "single pass" leads available from MEDTRONIC, INC. have been implanted to provide stimulation to sites in the stomach wall to treat chronic nausea and vomiting associated with gastroparesis. The unipolar electrode of these leads comprises a length of exposed lead conductor and is of the type disclosed in commonly assigned U.S. Pat. Nos. 5,425,751, 5,718,392 and 5,861,014. The above-referenced '039 patent and the '014 patent disclose the Model 4300 lead sewn through the serosa laterally into the muscularis externa to dispose the stimulation/sense electrode therein. A large incision is necessary to access the site, and a needle is used to perforate the serosa and muscularis externa laterally without fully penetrating the wall and to draw the stimulation/sense electrode into the muscularis externa. A laparascopic approach can be taken, but it is difficult to maneuver the needle to effect the fixation of the stimulation/sense electrode at the site. It is suggested in the '039 patent that two or more electrodes of this type can be formed along the length of the lead body that would be sewn laterally through and disposed within the muscularis externa.

The stimulation/sense electrodes conventionally employed in such gastrointestinal stimulation systems are formed of bio-compatible material shaped to either bear against the serosa or penetrate sub-serosally into the muscularis externa and polished to present an impervious outer surface. It is also suggested in the above-referenced '014 patent that the exposed electrode(s) of the single pass lead can alternatively be formed of other biocompatible electrode materials, including porous, platinized structures and could feature various pharmaceutical agents. Suggested pharmaceutical agents include dexamethasone sodium phosphate or beclomethasone phosphate in order to minimize the inflammatory response of the tissue to the implanted lead.

The above-referenced, commonly assigned, '326 patent shows a pin electrode mounted to extend orthogonally from a planar surface of a plate, wherein the pin electrode has a sharpened tip and is pressed through the serosa. The plate abuts against the serosa to limit the depth of penetration of the pin electrode to its length and has suture holes through it enabling the plate to be sutured to the GI tract wall to prevent dislodgement.

A further gastrointestinal lead bearing a pin electrode extending axially from the distal end of the lead body is disclosed in U.S. Pat. No. 5,423,872. In one version, the pin electrode is formed with distal tip retention barbs 21 that are pressed into the gastrointestinal wall and maintained in position by a suture passed through a suture pad. In a further version, more distally disposed and retractable barbs 37 are deployed to stabilize the pin electrode. In this variation, the lead body is formed with coaxial conductors to provide a bipolar lead, whereby a ring-shaped electrode 33 surrounds the distally and axially extending, pin electrode 31.

Thus, certain of the stimulation/sense electrodes that have been employed or disclosed in the above-referenced gastrointestinal stimulation systems are affixed in place by sutures, requiring surgical exposure of the GI tract wall at the site sufficient to enable suturing. In the case of the lead disclosed in the '872 patent, prevention of axial movement and perforation of the GI tract wall at the site of attachment cannot be assured by the limited engagement of the necessarily short and minute fixation barbs with the serosa or sub-serosa tissue. More robust fixation mechanisms are needed to avoid migration of the stimulation/sense electrode resulting either in dislodgement or perforation of the GI tract wall.

The above-described gastrointestinal leads have either unipolar electrodes or bipolar or multi-polar electrodes. The bipolar electrodes are typically disposed in close proximity to one another upon a single lead body or head or as sets of bipolar electrodes spaced apart along an elongated ribbon-like support as shown in the above-referenced '326 patent. It is generally desired to place individual electrodes of a bipolar electrode pair at least about 1.0 cm apart.

There are cases where the patient's stomach anatomy may not accommodate a lead that has two electrodes spaced apart by 1.0 cm or more in an axial arrangement along a lead body as suggested in the '039 patent or spaced apart by 1.0 cm or more on an electrode head or elongated ribbon-like support. For example, some patients have a jejunostomy feeding tube inserted into the stomach for supplemental nutrition, which may interfere with electrode placement, particularly relatively large electrode heads or elongated ribbon-like supports. This feeding tube is sometimes placed in the antrum of the stomach in the same location where it is desired to place electrodes to gastric stimulation for treatment of symptoms of gastroparesis. It is difficult to place bipolar electrodes in such a restricted area, and, when possible, the spacing between the electrodes may not be optimal.

Other patients may have had a surgical intervention, e.g., partial gastric resection for ulcer disease. In such cases, the remaining stomach may not be sufficiently large to place a bi-polar, single pass electrode of the type suggested in the above-referenced '039 patent into the circular muscle layer. And, the available surface area of the stomach to mount an electrode head or ribbon-like support of the types described above may not be available to locate the stimulation and/or sensing electrodes optimally.

Current neurostimulator IPGs are capable of operating with either unipolar or bipolar leads through bipolar connector sockets of the IPG header. If unipolar GI tract electrodes are employed to achieve the desired spacing in the affected regions, their proximal connector pins are each connected to one of the (typically) two available bipolar connector sockets of the neurostimulator IPG. Thus, when unipolar leads are employed, they restrict the number of stimulation/sense electrodes that could be employed with the neurostimulator IPG.

In the field of cardiac stimulation, cardiac pacing leads having bipolar and unipolar pace/sense electrodes have long been used in conjunction with pacing system IPGs to conduct pacing pulses generated by the IPG to a site of the heart and cardiac signals from the site to the IPG. Pacing leads are typically provided with a passive fixation or an active fixation mechanism at the lead body distal end that is passively or actively engaged with cardiac tissue to anchor a distal tip electrode at a desired site in or on the heart. Passive fixation generally involves an atraumatic fixation lodging the distal electrode against the endocardium or within a coronary blood vessel. Positive or active fixation generally involves a more traumatic penetration of a fixation mechanism into the myocardium from an endocardial or epicardial surface, and the active fixation mechanism commonly comprises a distal pace/sense electrode. Typically, the active fixation mechanism comprises the single pace/sense electrode or one of the bipolar pace/sense electrodes, but can be separate and electrically isolated from the pace/sense electrodes.

Endocardial pacing leads having either active fixation or passive fixation mechanisms are implanted by a transvenous route into a heart chamber to locate the distal pace/sense electrode(s) at a selected site in the heart chamber where an active or passive fixation mechanism is deployed to maintain the pace/sense electrode affixed at the site. Endocardial active fixation pacing leads typically employ extendable and retractable helixes or hooks that are retracted during introduction and are extended distally from the lead body distal end at the site of attachment as shown, for example, in commonly assigned U.S. Pat. No. 5,837,006.

Epicardial pacing leads are implanted by exposure of the epicardium of the heart through a limited thoracotomy. The distal end of the epicardial lead formed with one or two pace/sense electrodes and an active fixation mechanism supported by an electrode head is affixed to the epicardium. Active fixation mechanisms of epicardial pacing leads typically comprise a tissue penetrating, self-affixing mechanism extending away from a support or base or plate of the electrode head. The fixation mechanism is forced into the myocardium typically employing an insertion tool engaging the electrode head until it is fully seated within the endocardium and the plate bears against the epicardium. The plate is typically formed with a tissue ingrowth encouraging fabric or lattice, whereby tissue ingrowth about the plate assists in chronic anchoring to the heart.

One such active fixation, unipolar, epicardial pacing lead comprises the MEDTRONIC® Model 6917 and succeeding lead models that are disclosed in commonly assigned U.S. Pat. No. 3,737,579. The active fixation mechanism comprises a rigid helix having a sharpened tip that is coupled with a lead conductor within the electrode head and a helix axis. The helix is mounted to the electrode head such that the helix axis extends orthogonally to the plate. The distal electrode comprises an uninsulated portion of the helix. A bipolar version of leads of this type is disclosed in commonly assigned U.S. Pat. No. 4,010,758 wherein an annular or ring-shaped electrode is formed on the plate surface around the helix and coupled to a second lead conductor within the electrode head. Other variations of such unipolar or bipolar epicardial screw-in leads include multiple coaxial and intertwined helixes or a helix axially surrounding a pin extending coaxially with the helix axis from the electrode head. Other variations of such epicardial screw-in leads include multiple co-axial and intertwined helixes or a helix axially surrounding a pin extending coaxially with the helix axis from the electrode head, e.g., those shown in U.S. Pat. Nos. 4,235,246 and 4,452,254 and in UK Patent No. 1,277,107.

During implantation, the lead body and electrode head are mounted to an elongated tool, and the sharpened tip of the helix is advanced through the incision to perforate the epicardium. The tool and lead are rotated to screw the helix in until the plate abuts the epicardium, and the electrode head is detached from the tool.

A further epicardial screw-in lead is disclosed in commonly assigned U.S. Pat. No. 4,357,946 wherein the helix is mounted to a gear mechanism within the electrode head. The helix can itself be rotated to screw into the myocardium without rotating or moving the electrode head by a rotation of a removable stylet extending through the length of the lead body and engaging the gear mechanism. Both unipolar and bipolar embodiments are disclosed.

A further active fixation, unipolar, epicardial lead comprises the MEDTRONIC® Model 6951 lead disclosed in commonly assigned U.S. Pat. Nos. 4,313,448 and 4,424,818. The active fixation mechanism comprises forward facing barbed electrode having the tip at a predetermined angle with relation to the shank of the stimulation/sense electrode and with respect to a flexible base pad or plate of the electrode head. The plate has a substantially centered hole and a plurality of outer holes for fibrous ingrowth, and the shank of the stimulation/sense electrode extends out through the substantially centered hole. The barbed electrode is pushed into the myocardial tissue to the point where the base pad engages against the epicardium thereby indicating full implantation within the myocardium. During implantation, a stiffening stylet is employed to stiffen the lead body and a forceps is employed to grasp the electrode head to push the barb into the myocardium. A still further cardiac lead employing multiple hooks and a fixation tool for retracting the hooks during implantation is disclosed in U.S. Pat. No. 4,177,818.

Typically, cardiac pacing leads have a unitary lead body extending between a single distal pace/sense electrode or pair of pace/sense electrodes and a proximal connector assembly. However, bifurcated cardiac lead bodies extending to separate distal pace/sense electrodes are disclosed in U.S. Pat. Nos. 3,333,045, 3,472,234, 3,866,615, 4,000,745, 5,328,442, and 5,489,294.

Such active fixation, cardiac pacing leads with or without a bifurcated lead body have not, to our knowledge, been employed in the field of gastrointestinal stimulation. The myocardium is formed of muscle layers that are typically thicker and stiffer when pressed against than the muscle layers of the organ walls of the GI tract. The organ walls of the GI tract, e.g. the stomach wall, are thinner and more compliant and less massive than the heart wall, so they are difficult to prevent from simply collapsing when pressed against. The serosa is not a tough membrane that an electrode can catch in like the epicardium. Also, the overall mass of the heart is much greater than the stomach. For these reasons, it can be difficult to get anything like a hook or screw-in helix to penetrate the outer serosa of the GI tract, not perforate all the way through the GI tract wall and to stay affixed chronically.

SUMMARY OF THE INVENTION

The present invention is preferably embodied in a GI tract lead adapted to be implanted within the body at a site of the GI tract to conduct electrical stimulation from an implantable or external neurostimulator to the site and to conduct electrical signals of the GI tract from the site to the implantable or external neurostimulator.

In accordance with the present invention, the GI tract lead has a lead body comprising a common lead body trunk extending from a lead body trunk proximal end to a junction with a first plurality of lead body legs that extend from the junction to a like first plurality of lead body leg distal ends. An electrode head is formed at each lead body leg distal end having a stop or plate and supporting at least one stimulation/sense electrode and an active fixation mechanism, whereby a plurality of active fixation attachment mechanisms are supported by a like plurality of electrode heads. The plurality of electrode heads can be affixed by the fixation mechanism at a plurality of spaced apart locations of the GI tract. The plurality of electrode heads can be affixed spaced apart an optimal distance for efficacious sensing and/or stimulation accommodating the physiology and any defects or surgical interventions of the physiology or other therapeutic equipment or IMDs that restrict full access to the GI tract.

In a further aspect of the invention, a connector assembly at the lead body proximal end comprises a like plurality of connector elements that are each coupled through second plurality of lead conductors enclosed within the lead body that extend between a stimulation/sense electrode through a lead body leg and the lead body trunk to a proximal connector element of the connector assembly. The connector assembly is preferably a bipolar or multi-polar in-line connector adapted to be received in a compatible bipolar or multi-polar socket of a GI tract neurostimulator IPG. In this way, the number of GI tract sites where electrodes are affixed is maximized for a given neurostimulator IPG.

The active fixation mechanisms preferably extend away from the stop or plate of the electrode head and are shaped to penetrate through the serosa and into the muscularis externa upon application of penetrating force through the electrode head to the GI tract wall to draw the stop or plate against the serosa and operatively contact the stimulation/sense electrode with the GI tract wall. The stop or plate inhibits further advancement of the active fixation mechanism and perforation of the GI tract wall, and the active fixation mechanism cooperates with the stop or plate to inhibit dislodgement of the stimulation/sense electrode from operative contact with the GI tract wall.

The active fixation mechanisms are selected from helixes and barbed hooks having sharpened tips or free ends that perforate the serosa and lodge in the muscularis externa or the submucosa. The maximal depth of penetration of any part of the fixation mechanism from the stop or plate is preferably in the range of 1 mm to 15 mm when the site comprises the antrum or in the range of 1 mm to 10 mm when the site comprises corpus or fundus to ensure that the free end does not extend substantially through the stomach wall.

The helixes and hooks can be formed of biocompatible conductive materials that are coupled with the lead conductors and un-insulated at least in part to operate as the sensing and/or stimulation electrodes. The stimulation/sense electrode surface can be coated with a porous platinized structure to reduce polarization and/or an anti-inflammatory agent that inhibits inflammation that can negatively affect the ability to sense electrical signals of the GI tract or to efficiently deliver electrical stimulation. The anti-inflammatory agents can be embedded into a monolithic controlled release device (MCRD) carried by the electrode head.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

The bifurcated bipolar leads and methods of attachment and the GI tract stimulation system of the present invention provide the surgeon with more options for electrode placement about an area of interest of the GI tract compared to the leads, methods and systems previously employed in GI tract stimulation.

A GI tract stimulation system known in the prior art from the above-referenced '955 patent, for example, comprises a neurostimulator IPG having a plurality of leads extending to sensing and/or stimulation electrodes passed through the serosa and embedded into the GI-tract wall, e.g., the muscularis externa of the stomach wall, and held there by sutures. Each of the four leads illustrated in the '955 patent apparently comprises a unipolar lead coupled to a single connector socket of the neurostimulator IPG (requiring four sockets) or an in-line pair of stimulation/sense electrodes spaced apart along the portion of the lead body drawn through the muscularis externa.

Figure 1:
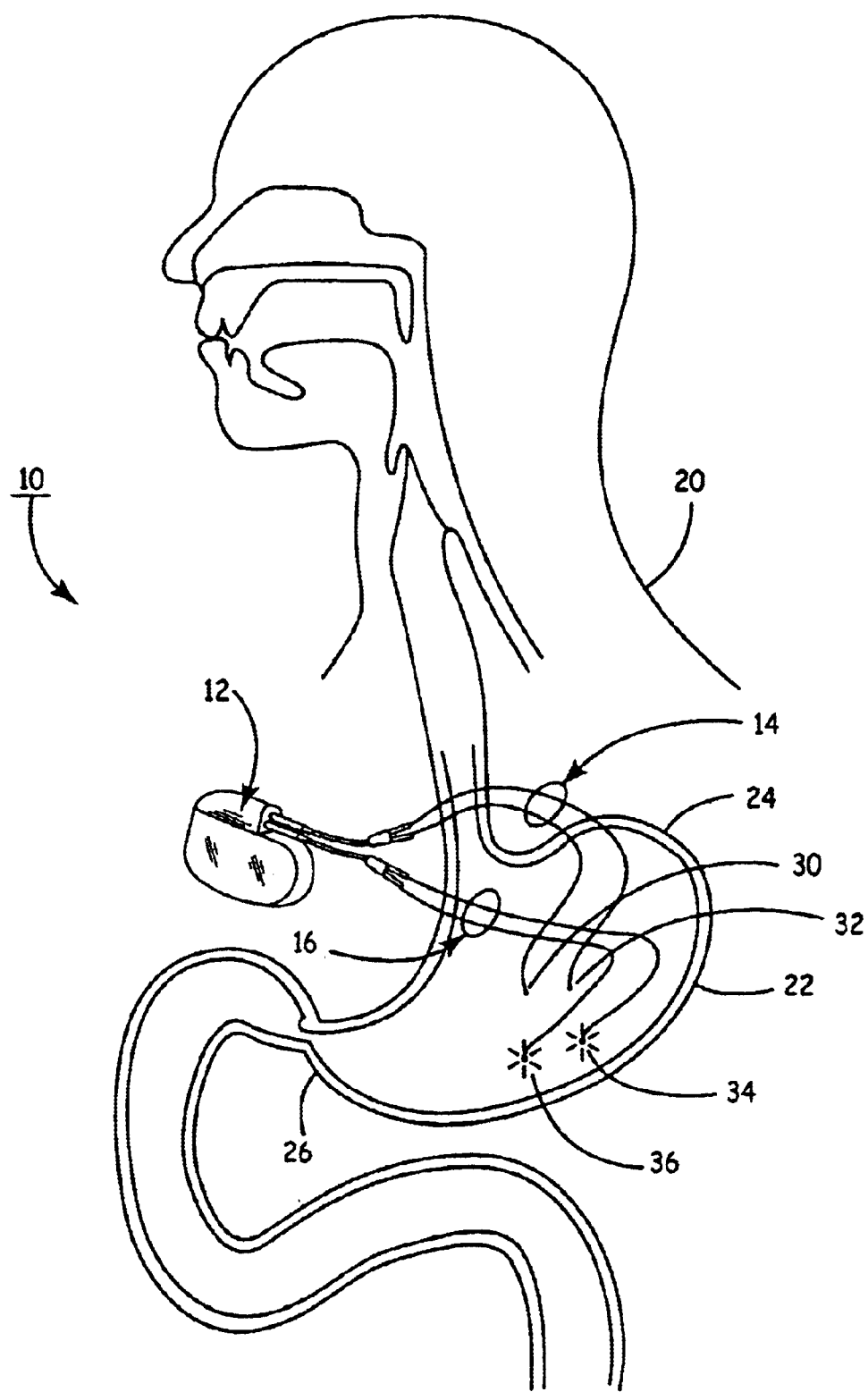
FIG. 1 is a schematic illustration of a GI tract stimulation system of the present invention employing the leads depicted in FIGS. 2–8.

By contrast, the bifurcated GI tract leads 14 and 16 of the present invention depicted in FIGS. 1–8 take advantage of the bipolar connector technology used with all neurostimulator IPGS, e.g., the IPG 12 of FIG. 1. In this way the number of stimulation/sense electrodes is maximized and their spacing apart is optimized. It will be understood that the lead electrodes may be affixed along or to any of the other structures and organ walls along the GI tract, including the colon, small intestine, stomach, or even the esophagus.

The bifurcated GI tract leads 14 and 16 of the present invention that are attached to such an IPG 12 employ active fixation mechanisms supported by electrode heads that penetrate the GI tract wall during to effect fixation. Insertion tools that grip the electrode heads or fixation mechanism and, in certain cases, the lead body are employed during implantation to embed the fixation mechanism of each electrode head through the serosa and substantially into the muscularis externa and thereby stabilize the stimulation/sense electrodes. The stimulation/sense electrodes can comprise the fixation mechanism or be separated from the fixation mechanism. The lead connector assembly at each lead body proximal ends is inserted into an IPG connector socket of the IPG 12 once the fixation is accomplished. The stimulation/sense electrodes of the GI tract leads 14 and 16 are shown in FIG. 1 coupled to the stomach wall through use of the positive or active fixation mechanisms of the present invention.

For example, the first bifurcated GI tract lead 14 extends to stimulation/sense electrodes 30 and 32 implanted against the serosa of stomach wall 24 in a first pair of locations, and the second bifurcated GI tract lead 16 extends to stimulation/ sense electrodes 34 and 36 implanted against the serosa of stomach wall 24 in a second pair of locations. In this way, each pair of stimulation/sense electrodes can be optimally spaced apart from one another and around any obstructions and used to either stimulate or sense or for both stimulation and sensing.

In the example shown in FIG. 1, the stimulation/sense electrodes 30 and 32 of the first bifurcated GI tract lead 14 are preferably implanted through the serosa at the area within the transition of the corpus and the antrum on the great curvature and are employed for applying gastro-stimulation pulses to the stomach wall at these locations. Of course, other locations of the stimulation/sense electrodes 30 and 32 of the first bifurcated GI tract lead 14 may be used, such as in the fundus 24, caudud corpus as well as the orad or terminal antrum 26. The stimulation/sense electrodes 34 and 36 of the second bifurcated GI tract lead 16 are used to conduct any gastro-electrical signals traversing these locations of the stomach 22 to the IPG 12. Preferably the stimulation/sense electrodes 34 and 36 of the second bifurcated GI tract lead 16 are positioned distally in the mid-antrum also along the great curvature, although these electrodes 34 and 36 may also be positioned in other locations.

The IPG 12 can comprise any of the hermetically enclosed IPGs disclosed in the above-listed patents that enclose a battery and an electrical operating system powered by a battery. Sense amplifiers of the IPG operating system sense the gastro-electrical signals conducted through the second set of electrodes 34 and 36, and pulse generator circuitry that generates electrical stimulation pulses that are conducted through the first set of electrodes 30 and 32 to the stomach 22 in accordance with a programmed operating mode and programmed operating parameter values. It will be understood that the stimulation/sense electrodes can all function as sensing and stimulation electrodes, and the selection of the stimulation/sense electrodes for sensing and stimulation functions can be programmed into the IPG 12.

Figure 2:
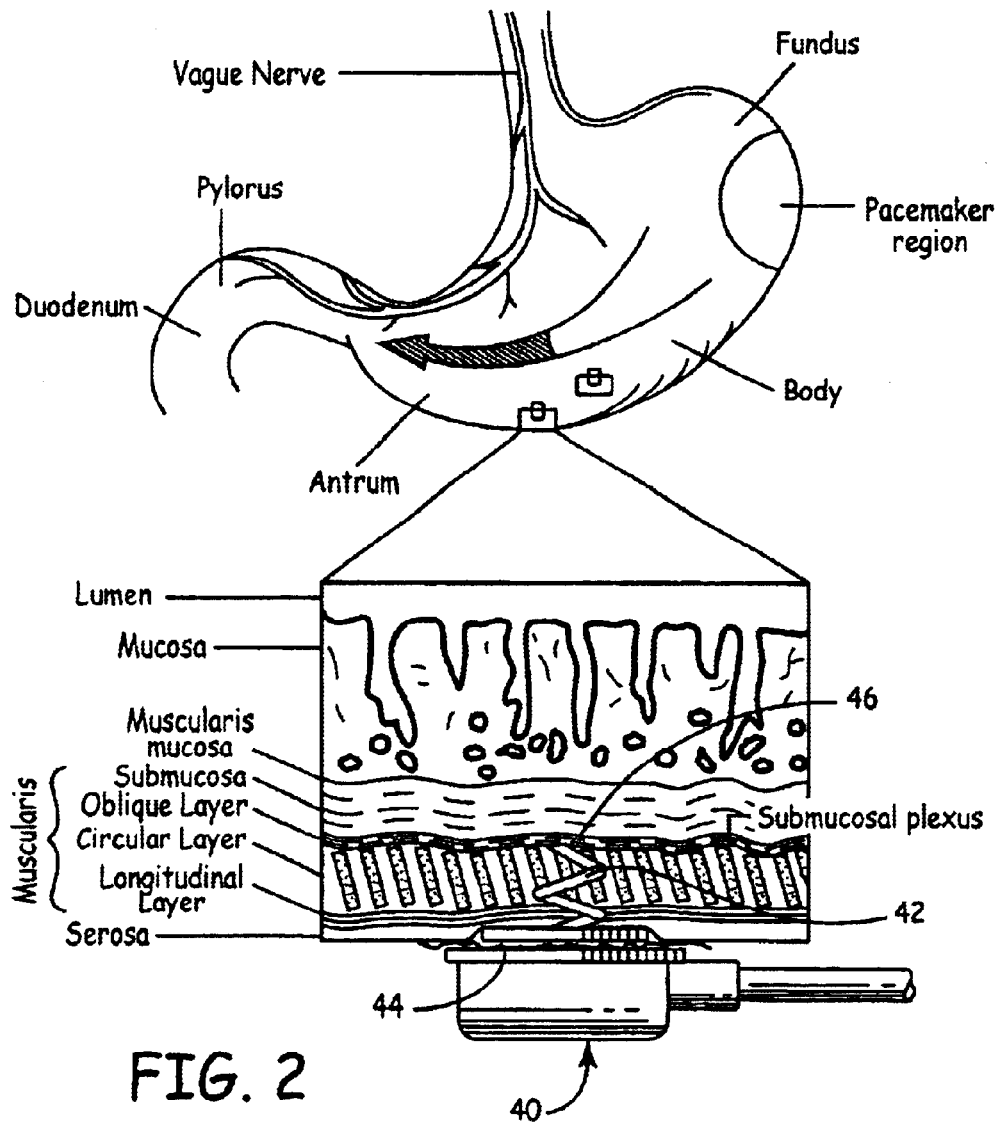
FIG. 2 is a detailed view of the stomach wall showing the affixation of an active screw-in electrode within the muscularis externa.
Figure 3:
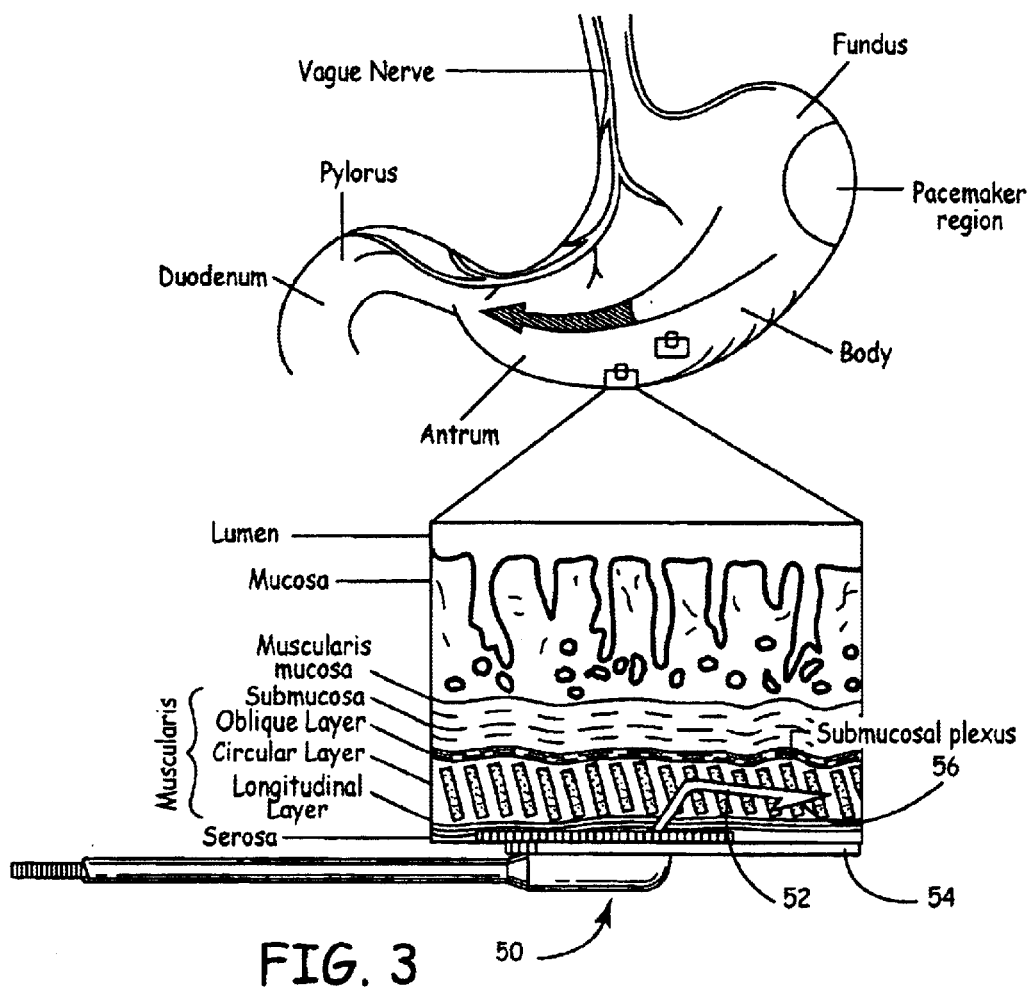
FIG. 3 is a detailed view of the stomach wall showing the affixation of an active hook electrode within the muscularis externa.

The stomach wall of the stomach 22 comprises essentially seven layers of tissue that are shown in cross-section in FIGS. 2 and 3. The seven tissue layers include the oblique, circular, and longitudinal muscle layers of the muscularis externa that contract and expand as described above, interposed between the interior stomach mucosa and the external serosa. In the preferred embodiments, the fixation mechanisms and electrodes of each lead perforate the serosa and lodge in the muscularis externa, particularly within the thickest circular layer as shown in FIGS. 2 and 3. The active fixation mechanisms are selected from helixes and barbed hooks having sharpened tips or free ends that perforate the serosa and lodge in the muscularis externa or the submucosa. The maximal depth of penetration of any part of the fixation mechanism from the plate is preferably in the range of 1 mm to 15 mm when the site comprises the antrum or in the range of 1 mm to 10 mm when the site comprises corpus or fundus to ensure that the free end does not extend substantially through the stomach wall.

Figure 8:
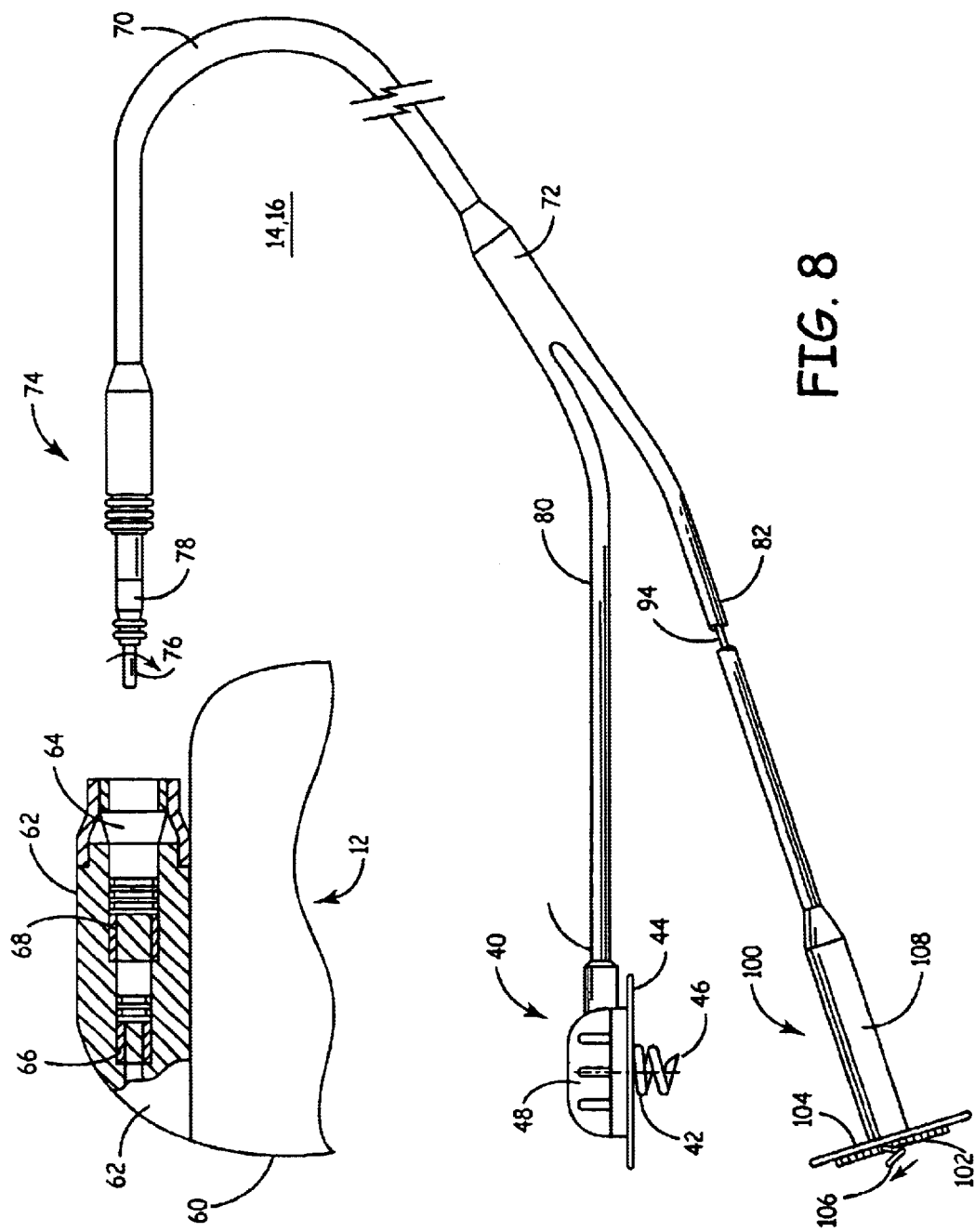
FIG. 8 is a plan view of a fifth bifurcated GI tract lead of the present invention.

FIG. 2 illustrates the preferred affixation of a combined fixation helix and electrode 42 of a screw-in electrode head 40 screwed through the serosa and into the muscularis externa until the electrode head plate 44 abuts the serosa. The combined fixation helix and electrode 42 can be fixed to the plate 44 so that the entire electrode head must be grasped and rotated to screw the helix free end through the serosa and to the depicted depth of the muscularis externa in the manner of the electrode head described in the above-referenced '737 patent or '579 patent or '758 patent, for example. Or, the combined fixation helix and electrode can be mounted to a rotatable mechanism inside the screw-in electrode head 40 that is rotated by a stylet in the manner described in the above-referenced '946 patent or by rotation of the lead conductor as described in the above-referenced '006 patent. Moreover, although the lead body leg is shown extending proximally away from the plate 44, parallel thereto, it will be understood that the lead body leg can extend away from screw-in electrode head at any convenient angle or be aligned at right angles to the plate 44 as shown in the embodiment of FIG. 8 described below.

FIG. 3 illustrates the preferred affixation of a combined fixation hook and electrode 52 pressed through the serosa and into the muscularis externa until the electrode head plate 54 of hook electrode head 50 abuts the serosa. The fixation hook and electrode 52 can be pressed through the serosa and into the muscularis externa employing a forceps grasping the electrode head 50 or a tool of the type disclosed in the above-referenced '818 patent.

The barbed hook 52 comprises a hook shank having a proximal shank portion that extends from the hook fixed end away from the hook plate 54 to an elbow joining a distal shank portion that extends generally in parallel with the hook plate 54 to the barbed tip 56. The bend can be selected to extend the proximal shank portion and barbed tip 58 toward or away from the hook plate 54 as shown in broken lines in FIG. 4. The shank portion can be insulated as also shown in FIGS. 4 and 5.

It should be understood that the shape of the hook 52 can be altered in many ways, and that the hook plate can support more than one such hook having hook shanks that extend in parallel to one another or toward one another in the manner of the those disclosed in the above-referenced '818 patent.

Thus, the active fixation mechanisms 42 and 52 extend away from the plates 44 and 54, respectively, of the screw-in electrode head 40 and the hook electrode head 50, respectively, and are shaped to penetrate through the serosa and into the muscularis externa upon application of penetrating force through the electrode heads 40 and 50. In each case, the plate 44 and 54 is drawn against the serosa and operatively contacts the stimulation/sense electrode with the stomach wall. The plate 44, 54 inhibits further advancement of the active fixation mechanism and perforation of the stomach wall, and the active fixation mechanism cooperates with the plate 44, 54 to inhibit dislodgement of the stimulation/sense electrode from operative contact with the stomach wall.

Figure 4:
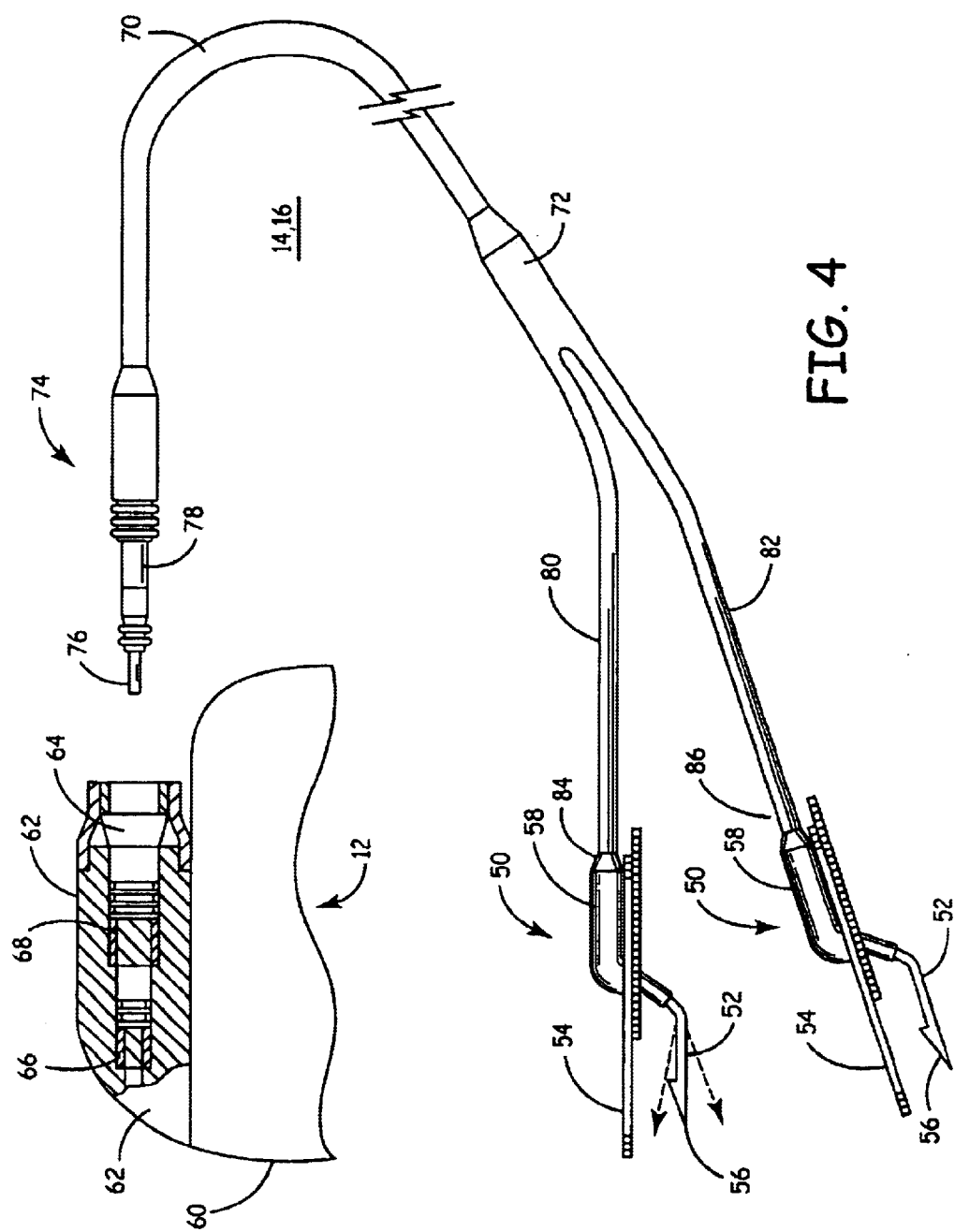
FIG. 4 is a plan view of a first bifurcated GI tract lead of the present invention.
Figure 5:
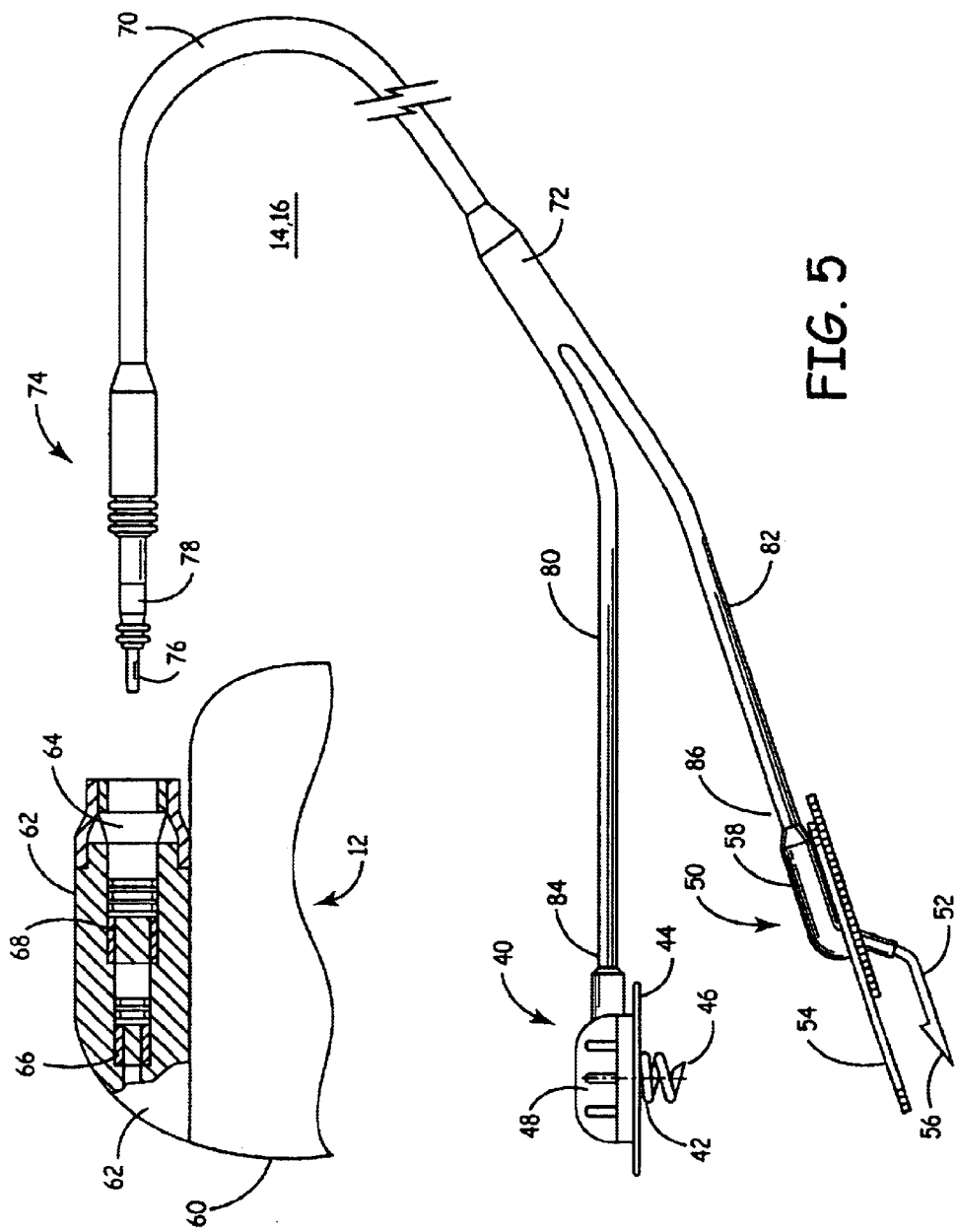
FIG. 5 is a plan view of a second bifurcated GI tract lead of the present invention.

The IPG 12 further comprises a hermetically sealed housing 60 enclosing the battery and electrical operating system and a connector header 62 shown in partial cross-section in FIGS. 4 and 5. A pair of bipolar connector sockets 64, 64' are formed in the connector header 62, each connector socket 64, 64' including IPG connector elements 66 and 68 that are electrically connected to circuitry within housing 60 through hermetically sealed feedthroughs in a manner well known in the art. Each bipolar connector socket 64, 64' receives a bipolar or unipolar lead connector assembly, e.g. depicted bipolar lead connector assembly 74, so that electrical connections are made between lead connector elements 76 and 78 and IPG connector elements 66 and 68, respectively, in a manner well known in the art.

FIGS. 4–8 illustrate exemplary GI tract leads 14, 16 of the present invention having a lead body extending between proximal connector assembly 74 and various combinations of screw-in and hook electrode heads 40 and 50 attached to the free distal ends 84 and 86 of the lead body. Each bifurcated lead 14, 16 illustrated in greater detail in FIGS.

4–8 comprises a common lead body trunk 70 extending from the lead connector assembly 74 at the lead body trunk proximal end to a junction 72 with a first plurality of lead body legs 80 and 82 that extend from the junction 72 to a like first plurality of lead body leg distal ends 84 and 86. The overall length of the lead body is preferably in the range of 10.0 cm to 50.0 cm, and the lead body legs are preferably at least 2.0 cm to 10.0 cm in length to provide a wide separation range between attachment sites.

An electrode head 40 or 50 is formed at each lead body leg distal end 84, 86, supporting a respective helical or hook fixation mechanism and electrode in one of the various configurations described above. The exposed electrode surface of each electrode of each such electrode head is connected electrically to a lead conductor extending from the electrode through one of the lead body legs 80 and 82 and through the common lead body trunk 70 to one of the lead connector elements 76 and 78.

Thus, FIG. 4 depicts a GI tract lead 14, 16 having first and second hook electrode heads 50 and 50' attached to the lead body leg distal ends 84 and 86, respectively. During implantation, the opposed head sides 58 of the first hook electrode head 50 are grasped by forceps or the first hook electrode head 50 is grasped by a tool of the type described in the above-referenced '818 patent. The tool is used to advance the first hook electrode head 50 to the first site of the stomach or other site of the GI tract and to press the hook tip 56 through the serosa until the plate 54 is seated against the serosa. The grasp exerted by the forceps or tool is then released, and the process is repeated to attach the second hook electrode head 50' at a second site of the stomach or other site of the GI tract.

This process is repeated to implant the second of the GI tract leads 14 and 16. Once satisfactory electrical test results are achieved, the proximal connector assembly 74 is inserted into the IPG connector head socket 64. Sutures can then be made through the plate of each implanted electrode head and underlying stomach or other GI tract wall to strengthen the attachment.

FIG. 5 depicts a GI tract lead 14, 16 comprising a screw-in electrode head 40 attached to the lead body leg distal end 84 and a hook electrode head 50 attached to the lead body leg distal end 86. In this case, the fixation helix 42 is fixed to the screw-in electrode head 40 so that the entire lead 14, 16 must be rotated to rotate the fixation helix 42. Thus, during implantation, the opposed sides 48 of the screw-in electrode head 40 are grasped by a screw-in lead insertion tool of the type described in the above-referenced '737 patent, for example, and the lead body may be supported by the tool. The tool is used to advance the screw-in electrode head 40 to the first site of the stomach or other site of the GI tract, to press the helix tip 46 into the serosa, and to rotate the helix 42 into the muscularis externa until the plate 44 is seated against the serosa. Then, the screw-in electrode head 40 and lead body are released from the screw-in lead insertion tool. The hook electrode head sides 58 of the hook electrode head 50 are grasped by forceps or the hook electrode head 50 is grasped by a tool of the type described in the above-referenced '818 patent. The tool is used to advance the hook electrode head 50 to the second site of the stomach or other site of the GI tract and to press the hook tip 56 through the serosa until the plate 54 is seated against the serosa. The forceps or tool is then released from the hook electrode head 50, and stimulation and/or electrical measurements are made through the pair of electrodes to ascertain that the sites of attachment are suitable.

Again, this process is repeated to implant the second of the GI tract leads 14 and 16. Once satisfactory electrical test results are achieved, the proximal connector assembly 74 is inserted into the IPG connector head socket 64. Sutures can then be made through the plate of each implanted electrode head and underlying stomach or other GI tract wall to strengthen the attachment.

Figure 6:
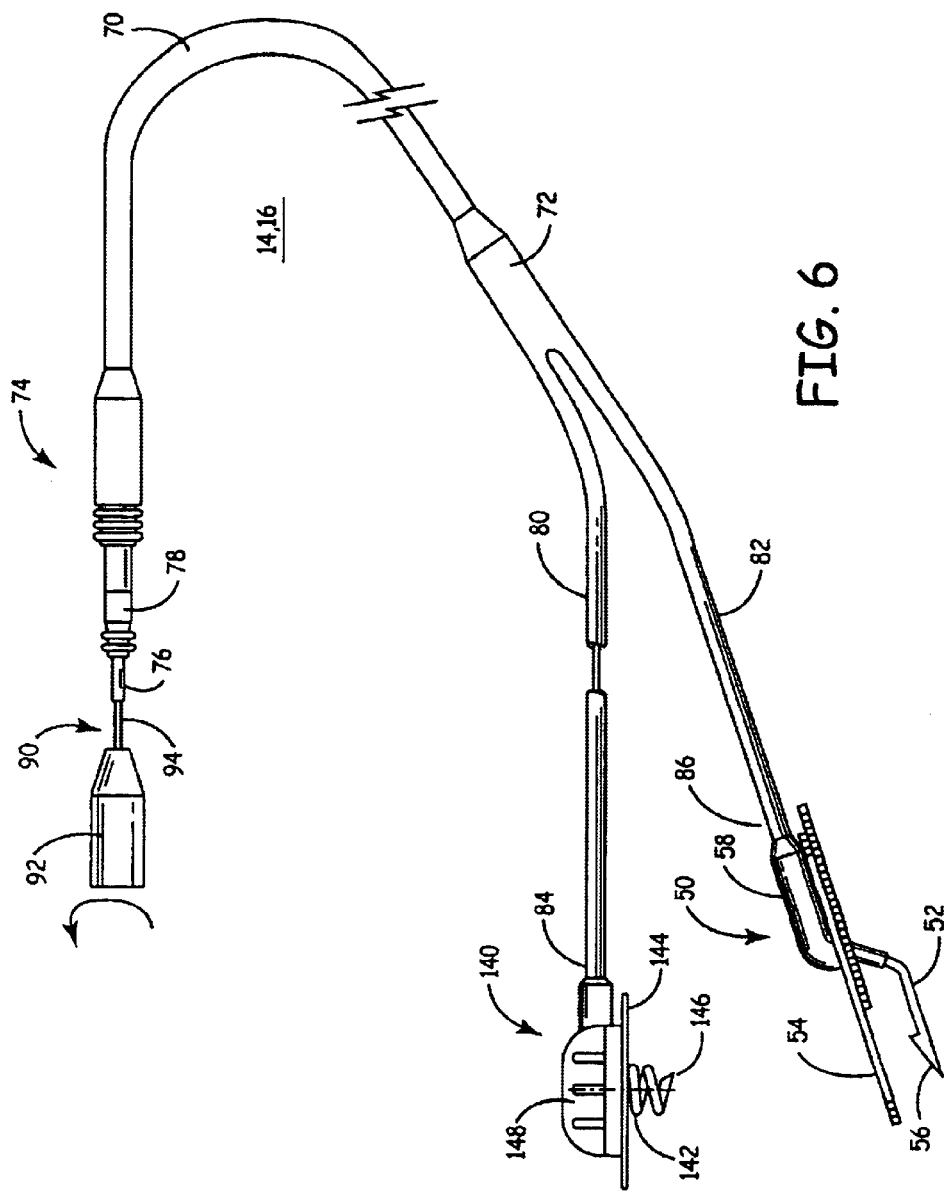
FIG. 6 is a plan view of a third bifurcated GI tract lead of the present invention.

FIG. 6 depicts a GI tract lead 14, 16 similar to that depicted in FIG. 5, except that the lead body encloses a stylet lumen extending axially from a proximal lumen end opening in the pin connector element 76 through the lead body trunk 70, the junction 72, the lead body leg 80, and into a screw rotation mechanism of the type disclosed in the above-referenced '946 patent enclosed within a rotatable screw-in electrode head 140. An elongated stylet wire 94 of a stylet 90 is inserted through the stylet lumen so that the stylet wire distal end engages the screw rotation mechanism that is attached to the fixed end of rotatable helix 142. The electrode head sides 148 are grasped by an insertion tool to direct the electrode head plate 44 toward or against the serosa at the desired implantation site. The handle 92 is rotated as the electrode head is held steady so that the stylet wire 94 rotates the helix 142 and screws it's sharpened tip 146 into the muscularis externa until the plate 144 abuts the serosa. The rotatable helix 142 can either be fully exposed or can be encased within the rotatable screw-in electrode head 140 and advanced from it during rotation by the stylet 90. The implantation of the GI tract lead 14, 16 of FIG. 6 follows the same implantation process as described above with respect to the lead 14, 16 depicted in FIG. 5.

Figure 7:
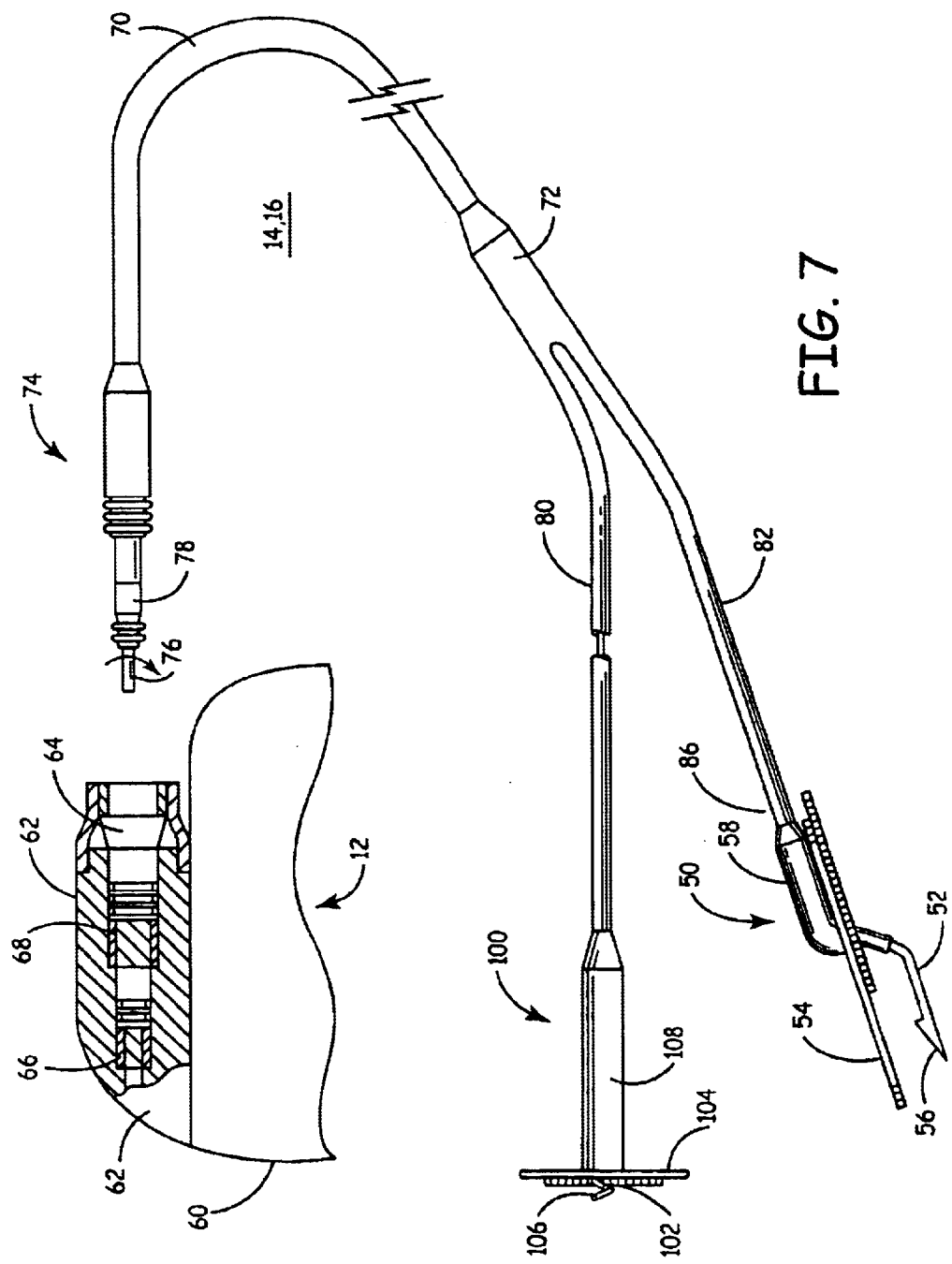
FIG. 7 is a plan view of a fourth bifurcated GI tract lead of the present invention.

An axially aligned screw-in electrode head 100 is depicted in FIGS. 7 and 8, wherein the helix 102 extends in axial alignment with the lead body, can be employed in a further embodiment of the GI tract leads 14 and 16. In this embodiment of the GI tract leads 14, 16, the lead body extends from the proximal connector assembly 74 through the lead body trunk 70, the junction 72, and lead body leg 80 to a screw-in electrode head 100 of the type disclosed in the above-referenced '006 patent. An inner, coiled wire conductor extends through a lead lumen extending from pin connector element 76 through the lead body trunk 70, the junction 72, and lead body leg 80 to a screw-in electrode head 100. The distal end of the coiled wire conductor is attached to a rotatable helix 102 within screw-in electrode head 100. The pin connector element 76 is rotatable with respect to the proximal connector assembly 74 to impart rotation torque through the lead conductor to rotate the helix 102 out of or back into the screw-in electrode head 100. The electrode head side 108 is grasped by an insertion tool to direct the electrode head plate 104 toward or against the serosa at the desired implantation site. The pin connector element 76 is rotated while the rotatable electrode head 100 is held steady to rotate the tip 106 and helix 102 to thereby screw them into the muscularis externa until the electrode head plate 104 engages against the serosa. The rotatable helix 102 can either be fully exposed or can be encased within the rotatable screw-in electrode head 100 and advanced from it during rotation of the pin connector element 76.

The implantation of the GI tract lead 14, 16 of FIG. 7 follows the implantation process as described above with respect to the lead 14, 16 depicted in FIG. 6, wherein either of the electrode heads 50 or 100 of FIG. 7 can be implanted first and the other electrode head second. The implantation of the lead 14, 16 of FIG. 8 follows the implantation process as described above with respect to the leads 14, 16 of FIG. 5, wherein the fixed screw-in electrode head 40 is implanted first and the rotatable screw-in-lead head 100 is implanted second.

Of course, a rotatable screw-in electrode head 140 in the embodiment depicted in FIG. 8 can replace the rotatable screw-in electrode head 100. Again, the implantation process as described above with respect to the leads 14, 16 of FIG. 5, wherein the fixed screw-in electrode head 40 is implanted first and the rotatable screw-in-lead head 140 is implanted second.

The electrode head plates 44, 54, 104 and 144 can comprise a fabric mesh disc of DACRON or other biocompatible material or a silicone rubber disc or a combination of both that is flexible, biocompatible, and encourages tissue growth adhesion with the serosa of the GI tract wall. The plates 44, 54, 104, 124, 144 can be substantially planar when unrestrained as depicted in the figures or may have any other convenient curvilinear shape that operates as a stop. In addition, once the attachment is made, it is possible to reinforce the attachment by suturing the plates 44, 54, 104, 144 to the stomach wall, placing the sutures either through the flexible plate or preformed suture holes in the plates 44, 54, 104, 144.

The helixes 42, 102, 142 and hooks 52 can be formed of bio-compatible conductive materials that are coupled with the lead conductors and un-insulated at least in the portion embedded in the muscularis externa to operate as the sensing and/or stimulation electrodes. Alternatively, the helixes 42, 102, 142 and hook 52 can simply provide fixation, and the stimulation/sense electrode can be formed on the surfaces of plates 44, 104, 144 and 54 that contacts the serosa. In any of these embodiments, the stimulation/sense electrode surface can be coated with a porous platinized structure to reduce polarization and/or an anti-inflammatory agent that inhibits inflammation that can negatively affect the ability to sense electrical signals of the GI tract or to efficiently deliver electrical stimulation. The anti-inflammatory agents can be coated onto the fixation mechanism or embedded into the insulation covering a portion of the fixation mechanism or into an MCRD carried by the electrode head, particularly in the surface of the plates 44, 104, 144, and 54. Such anti-inflammatory agents include steroids, anti-bacterial agents, baclofen, dexamethasone sodium phosphate and beclomethasone phosphate.

While above described embodiments comprise GI tract leads that fit within bipolar IPG connector assemblies, it will be understood that the present invention can be applied to any multi-polar IPG connector assemblies.

Moreover, while the junction 72 is fixed, in the above-described embodiments, to the lead body trunk 70 and legs 80, 82, it would be possible to provide a.

Y-connector at junction block 72 to enable separate attachment of unipolar GI tract lead connectors to the Y-connector at junction 72 after the GI tract lead electrode is affixed to the site of the GI tract. In this way, unipolar leads having any of the electrode heads 40, 50, 100 and 140 could be selected, the electrode heads attached at the desired sites, the lead connectors coupled to the Y-connector at junction 72, and the lead connector assembly 74 inserted into the IPG connector socket 64.

It should also be noted that the lead bodies of the bifurcated GI tract leads of the present invention could include first and second rotatable helix electrode heads 100 or 140 coupled to the distal ends 84 and 86 of the first and second lead body legs 80 and 82, respectively. In this case, plural lead body lumens extend from junction 72 through both of the lead body legs 80 and 82 and the lead body legs.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of GI tract neurostimulators are not disclosed and are not necessary to the practice of the present invention. In addition, it will be understood that specifically described structures, functions and operations set forth in the above-referenced patents can be practiced in conjunction with the present invention, but they are not essential to its practice.

Thus, embodiments of the IMPLANTABLE BIFURCATED GASTROINTESTINAL LEAD WITH ACTIVE FIXATION are disclosed. One skilled in the art will appreciate that the present invention can be practiced with embodiments other than those disclosed. The disclosed embodiments are presented for purposes of illustration and not limitation, and the present invention is limited only by the claims that follow.

It is therefore to be understood, that within the scope of the appended claims, the invention may be practiced otherwise than as specifically described without actually departing from the spirit and scope of the present invention.

What is claimed is:

1. A gastrointestinal lead adapted to be implanted within the body to conduct electrical stimulation from an implantable or external gastrointestinal stimulator to a site of the GI tract and to conduct electrical signals of the GI tract from the site to the implantable or external gastrointestinal stimulator comprising:

an elongated lead body comprising a common lead body trunk extending from a lead body trunk proximal end to a junction with a plurality of lead body legs that extend from the junction to a like plurality of lead body leg distal ends;

an electrode head formed at each lead body leg distal end having a plate and supporting at least one stimulation/sense electrode and an active fixation mechanism whereby a plurality of active fixation attachment mechanisms are supported by a plurality of electrode heads;

a connector assembly at the lead body proximal end comprising a plurality of connector elements; and a plurality of lead conductors enclosed within the lead body, each lead conductor extending between a stimulation/sense electrode through a lead body leg and the lead body trunk to a proximal connector element of the connector assembly, wherein each active fixation mechanism extends away from the plate of the electrode head and is shaped to penetrate through the serosa and into the muscularis externa upon application of force to the electrode head to draw the plate against the serosa and operatively contact the stimulation/sense electrode with the GI tract wall, whereby the plate inhibits further advancement of the active fixation mechanism and perforation of the GI tract wall and the active fixation mechanism inhibits dislodgement of the stimulation/sense electrode from operative contact with the GI tract wall.

2. The gastrointestinal lead of claim 1, wherein;

one active fixation mechanism comprises a helix comprising one or more coil turn extending from a helix fixed end and a helix free end and having a helix axis, the helix fixed end supported at the plate to extend the helix axis orthogonally to the plate, the helix free end adapted to penetrate through the serosa and the helix adapted to advance into the muscularis externa upon rotation of the helix until the plate is drawn against the serosa.

3. The gastrointestinal lead of claim 2, wherein the helix has an axial length enabling a depth of penetration from the plate in the range of 1 mm to 15 mm when the site comprises the antrum of the stomach wall or in the range of 1 mm to 10 mm when the site comprises corpus or fundus of the stomach wall to ensure that the helix free end does not extend substantially through the stomach wall.

4. The gastrointestinal lead of claim 2, wherein the stimulation/sense electrode is supported on the plate of the electrode head to bear against the serosa when the plate is drawn against the serosa.

5. The gastrointestinal lead of claim 2, wherein:
the helix is formed of a conductive electrode material; and
the helix fixed end is electrically coupled to a distal end of the lead conductor,
whereby the stimulation/sense electrode comprises at least a portion of the helix that is embedded substantially within the muscularis externa when the plate is drawn against the serosa.

6. The gastrointestinal lead of claim 2, wherein:
the helix is formed of a conductive electrode material;
a layer of insulation is formed over a first portion of the helix;
the helix fixed end is electrically coupled to a distal end of the lead conductor,
whereby the stimulation/sense electrode comprises at least an uninsulated second portion of the helix that is embedded substantially within the muscularis externa when the plate is drawn against the serosa.

7. The gastrointestinal lead of claim 2, wherein the helix fixed end is fixedly attached to the plate, and the electrode head is shaped to be engaged by a fixation tool that is manipulated to rotate the electrode head and helix.

8. The gastrointestinal lead of claim 7, wherein:
the elongated lead body encloses a stylet lumen extending through a lead body trunk and at least a second lead body leg into a second electrode head located at the distal end of the second lead body leg; and
the second electrode head comprises:
a helix comprising one or more coil turn extending from a helix fixed end and a helix free end and having a helix axis; and
a rotatable mechanism fitted into the electrode head and attached to the helix fixed end to extend the helix axis orthogonally to the plate, the rotatable mechanism adapted to be engaged by a stylet advanced through the stylet lumen, whereby the rotatable mechanism is rotated by the stylet to rotate the helix and advance the helix free end through the serosa and into the muscularis externa until the plate is drawn against the serosa.

9. The gastrointestinal lead of claim 2, wherein:
the elongated lead body encloses a stylet lumen extending through a lead body trunk and at least one lead body leg to the electrode head located at the distal end of the lead body leg supporting the helix; and
the electrode head comprises a rotatable mechanism fitted into the electrode head and attached to the helix fixed end to extend the helix axis orthogonally to the plate, the rotatable mechanism adapted to be engaged by a stylet advanced through the stylet lumen, whereby the rotatable mechanism is rotated by the stylet to rotate the helix and advance the helix free end through the serosa and into the muscularis externa until the plate is drawn against the serosa.

10. The gastrointestinal lead of claim 2, wherein another active fixation mechanism of the plurality of active fixation mechanisms comprises a hook comprising a hook shaft extending from a hook fixed end attached to an electrode head to a hook free end spaced from the plate, a sharpened tip and barb formed at the hook free adapted to penetrate through the serosa and to advance into the muscularis externa when insertion force is applied to the electrode head until the plate is drawn against the serosa, whereupon advancement of the hook free end is halted and the barb engages the muscularis externa to inhibit retraction of the hook.

11. The gastrointestinal lead of claim 1, wherein at least one active fixation mechanism comprises a hook comprising a hook shaft extending from a hook fixed end attached to an electrode head to a hook free end spaced from the plate, a sharpened tip and barb formed at the hook free adapted to penetrate through the serosa and to advance into the muscularis externa when insertion force is applied to the electrode head until the plate is drawn against the serosa, whereupon advancement of the hook free end is halted and the barb engages the muscularis externa to inhibit retraction of the hook.

12. The gastrointestinal lead of claim 11, wherein the stimulation/sense electrode is supported on the plate of the electrode head to bear against the serosa when the plate is drawn against the serosa.

13. The gastrointestinal lead of claim 11, wherein:
the hook is formed of a conductive electrode material; and
the hook fixed end is attached to a distal end of the lead conductor,
whereby the stimulation/sense electrode comprises at least a portion of the hook that is embedded substantially within the muscularis externa when the plate is drawn against the serosa.

14. The gastrointestinal lead of claim 11, wherein:
the hook is formed of a conductive electrode material;
a layer of insulation is formed over a first portion of the hook;
the hook fixed end is attached to a distal end of the lead conductor,
whereby the stimulation/sense electrode comprises at least an uninsulated second portion of the hook that is embedded substantially within the muscularis externa when the plate is drawn against the serosa.

15. The gastrointestinal lead of claim 14, wherein the plate is substantially planar and the hook shaft comprises a first portion extending from the hook fixed end at a first predetermined angle away from the plate and a second portion extending to the hook free end at a second predetermined angle.

16. The gastrointestinal lead of claim 11, wherein the plate is substantially planar and the hook shaft comprises a first portion and a second portion joined at a bend, the first portion extending from the hook fixed end to the bend at a first predetermined angle away from the plate and a second portion extending from the bend to the hook free end at a second predetermined angle selected to locate the hook free end further away from the plate than the bend.

17. The gastrointestinal lead of claim 11, wherein the plate is substantially planar and the hook shaft comprises a first portion and a second portion joined at a bend, the first portion extending from the hook fixed end to the bend at a first predetermined angle away from the plate and a second portion extending from the bend to the hook free end at a second predetermined angle selected to locate the hook free end closer to the plate than the bend.

18. The gastrointestinal lead of claim 11, wherein the plate is substantially planar and the hook shaft comprises a first portion extending from the hook fixed end at a first predetermined angle away from the plate and a second portion extending to the hook free end at a second predetermined angle.

19. The gastrointestinal lead of claim 11, wherein the electrode head is shaped to be engaged by a fixation tool that is manipulated to apply the insertion force to advance the hook free end through the serosa and into the muscularis externa.

20. The gastrointestinal lead of claim 11, wherein the hook free end is distanced from the plate enabling a depth of penetration from the plate in the range of 1 mm to 15 mm when the site comprises the antrum of the stomach wall or in the range of 1 mm to 10 mm when the site comprises corpus or fundus of the stomach wall to ensure that the helix free end does not extend substantially through the stomach wall.

21. The gastrointestinal lead of claim 1, wherein at least one electrode is supported on the plate of the electrode head to bear against the serosa when the plate is drawn against the serosa.

22. The gastrointestinal lead of claim 1, wherein:
at least one active fixation mechanism is formed of a conductive electrode material; and
the active fixation mechanism is electrically coupled to a distal end of the lead conductor,
whereby the stimulation/sense electrode comprises at least a portion of the active fixation mechanism that is embedded substantially within the muscularis externa when the plate is drawn against the serosa.

23. The gastrointestinal lead of claim 1, wherein:
at least one active fixation mechanism is formed of a conductive electrode material;
a layer of insulation is formed over a first portion of the active fixation mechanism;
the active fixation mechanism is electrically coupled to a distal end of the lead conductor,
whereby the stimulation/sense electrode comprises at least an uninsulated second portion of the active fixation mechanism that is embedded substantially within the muscularis externa when the plate is drawn against the serosa.

24. The gastrointestinal lead of claim 1, wherein:
the elongated lead body encloses a stylet lumen extending through a lead body trunk and at least one lead body leg to an electrode head located at the distal end of the lead body leg;
at least one fixation mechanism comprises a helix comprising one or more coil turn extending from a helix fixed end and a helix free end and having a helix axis; and
the electrode head comprises a rotatable mechanism fitted into the electrode head and attached to the helix fixed end to extend the helix axis orthogonally to the plate, the rotatable mechanism adapted to be engaged by a stylet advanced through the stylet lumen, whereby the rotatable mechanism is rotated by the stylet to rotate the helix and advance the helix free end through the serosa and into the muscularis externa until the plate is drawn against the serosa.

25. The gastrointestinal lead of claim 1, wherein:
at least one fixation mechanism comprises a helix comprising one or more coil turn extending from a helix fixed end and a helix free end and having a helix axis;
the elongated lead body encloses a conductor lumen extending through a lead body trunk and at least one lead body leg to the electrode head located at the distal end of the lead body leg supporting the helix; and
the lead conductor extends from a lead connector element through the conductor lumen and to the helix fixed end, whereby rotation of the lead connector element with respect to the lead connector assembly rotates the lead conductor and helix attached thereto with respect to the plate to advance the helix free end through the serosa and into the muscularis externa until the plate is drawn against the serosa.

26. The gastrointestinal lead of claim 1, wherein the plurality of active fixation mechanisms each comprise a hook comprising a hook shaft extending from a hook fixed end attached to an electrode head to a hook free end spaced from the plate, a sharpened tip and barb formed at the hook free adapted to penetrate through the serosa and to advance into the muscularis externa when insertion force is applied to the electrode head until the plate is drawn against the serosa, whereupon advancement of the hook free end is halted and the barb engages the muscularis externa to inhibit retraction of the hook.

27. The gastrointestinal lead of claim 1, wherein an anti-inflammatory material selected from the group consisting of steroids anti-bacterial agents, baclofen, dexamethasone sodium phosphate or beclomethasone phosphate is incorporated into the electrode head or fixation mechanism.

28. The gastrointestinal lead of claim 1, wherein the plurality of lead body legs are permanently connected to the common lead body at the junction.

29. The gastrointestinal lead of claim 1, wherein the plurality of lead body legs are removably connected to the common lead body at the junction.

30. A method of providing gastrointestinal sensing and/or stimulation through a gastrointestinal lead and a gastrointestinal stimulator comprising:
providing an elongated gastrointestinal lead body comprising a common lead body trunk extending from a connector assembly at a lead body proximal end comprising a plurality of connector elements of a lead connector assembly to a junction with a plurality of lead body legs that extend from the junction to a like plurality of lead body leg distal ends, an electrode head formed at each lead body leg distal end having a plate and supporting at least one stimulation/sense electrode and an active fixation mechanism, whereby a plurality of active fixation attachment mechanisms are supported by a plurality of electrode heads, and a plurality of lead conductors enclosed within the lead body, each lead conductor extending between a stimulation/sense electrode through a lead body leg and the lead body trunk to a proximal connector element of the connector assembly;
determining first and second gastrointestinal implantation sites optimally spaced apart for stimulation and/or sensing;
extending a first electrode head supporting a first active fixation mechanism to a first gastrointestinal implantation site;

deploying the first active fixation mechanism extending away from the plate of the electrode head and penetrating through the serosa and into the muscularis externa to draw the plate against the serosa and operatively contact the stimulation/sense electrode with the GI tract wall, whereby the plate inhibits further advancement of the active fixation mechanism and perforation of the GI tract wall and the active fixation mechanism inhibits dislodgement of the stimulation/sense electrode from operative contact with the GI tract wall;

extending a second electrode head supporting a second active fixation mechanism to a second gastrointestinal implantation site spaced from;

deploying the second active fixation mechanism extending away from the plate of the electrode head and penetrating through the serosa and into the muscularis externa to draw the plate against the serosa and operatively contact the stimulation/sense electrode with the GI tract wall, whereby the plate inhibits further advancement of the active fixation mechanism and perforation of the GI tract wall and the active fixation mechanism inhibits dislodgement of the stimulation/sense electrode from operative contact with the GI tract wall;

coupling the lead connector assembly to a gastrointestinal stimulator connector assembly of an implantable or external gastrointestinal stimulator to conduct electrical stimulation from the implantable or external gastrointestinal stimulator between the first and second sites of the GI tract and to conduct electrical signals of the GI tract from the first and second sites to the implantable or external gastrointestinal stimulator.

31. The method of claim 30, wherein;
the first active fixation mechanism comprises a helix comprising one or more coil turn extending from a helix fixed end and a helix free end and having a helix axis, the helix fixed end supported at the plate to extend the helix axis orthogonally to the plate; and
the deploying step comprises
pressing the helix free end through the serosa; and
rotating the helix to advance the helix into the muscularis externa until the plate is drawn against the serosa.

32. The method of claim 31, wherein the helix has an axial length enabling a depth of penetration from the plate in the range of 1 mm to 15 mm when the site comprises the antrum of the stomach wall or in the range of 1 mm to 10 mm when the site comprises corpus or fundus of the stomach wall to ensure that the helix free end does not extend substantially through the stomach wall.

33. The method of claim 31, wherein the stimulation/sense electrode is supported on the plate of the electrode head to bear against the serosa when the plate is drawn against the serosa.

34. The method of claim 31, wherein:
the helix is formed of a conductive electrode material; and
the helix fixed end is electrically coupled to a distal end of the lead conductor;
whereby the stimulation/sense electrode comprises at least a portion of the helix that is embedded substantially within the muscularis externa when the plate is drawn against the serosa.

35. The method of claim 31, wherein:
the helix is formed of a conductive electrode material;
a layer of insulation is formed over a first portion of the helix;
the helix fixed end is electrically coupled to a distal end of the lead conductor,
whereby the stimulation/sense electrode comprises at least an uninsulated second portion of the helix that is embedded substantially within the muscularis externa when the plate is drawn against the serosa.

36. The method of claim 31, wherein the helix fixed end is fixedly attached to the plate, and the rotating step comprises:
engaging the electrode head by a fixation tool; and
rotating the fixation tool to rotate the lead body, the electrode head and the helix to advance the helix substantially into the muscularis externa until the plate is drawn against the serosa.

37. The method of claim 31, wherein the rotating step comprises:
engaging the helix by a fixation tool; and
rotating the fixation tool to rotate the helix with respect to the lead body and the electrode head to advance the helix substantially into the muscularis externa until the plate is drawn against the serosa.

38. The method of claim 31, wherein:
the elongated lead body encloses a conductor lumen extending through the lead body trunk and the first lead body leg to the first electrode head located at the distal end of the first lead body leg supporting the helix;
the lead conductor extends from a lead connector element through the conductor lumen and to the helix fixed end, and
the rotating step comprises rotating the lead connector element with respect to the lead connector assembly to rotate the helix attached thereto with respect to the plate to advance the helix free end through the serosa and substantially into the muscularis externa until the plate is drawn against the serosa.

39. The method of claim 31, wherein:
the first electrode head encloses a rotatable mechanism for supporting the helix fixed end;
the elongated lead body encloses a stylet lumen extending through the lead body trunk and the first lead body leg to the first electrode head located at the distal end of the first lead body leg supporting the helix; and
the rotating step comprises:
inserting a stylet wire having through the stylet lumen to engage the rotatable mechanism; and
rotating the lead stylet with respect to the lead connector assembly to rotate the helix attached to the rotatable mechanism with respect to the plate to advance the helix free end through the serosa and substantially into the muscularis externa until the plate is drawn against the serosa.

40. The method of claim 31, wherein:
the second active fixation mechanism comprises a hook comprising a hook shaft extending from a hook fixed end attached to the second electrode head to a hook free end spaced from the plate of the second electrode head terminating in a sharpened tip and barb; and
the second deploying step comprises
engaging the second electrode head by a second fixation tool; and
applying force through the second fixation tool to press the hook free end through the serosa and lodge the hook substantially into the muscularis externa until the plate is drawn against the serosa.

41. The method of claim 30, wherein;

the first active fixation mechanism comprises a first helix comprising one or more coil turn extending from a first helix fixed end and a first helix free end and having a first helix axis, the first helix fixed end supported at and fixed to the plate to extend the first helix axis orthogonally to the plate;

the second active fixation mechanism comprises a second helix comprising one or more coil turn extending from a second helix fixed end and a second helix free end and having a second helix axis, the second helix fixed end supported by a rotatable mechanism of the electrode head to extend the second helix axis orthogonally to the plate;

the first deploying step comprises:
engaging the first electrode head by a first fixation tool;
pressing the first helix free end through the serosa; and
rotating the first fixation tool to rotate the lead body, the electrode head and the first helix to advance the first helix substantially into the muscularis externa until the plate is drawn against the serosa;

wherein the second deploying step comprises:
engaging the second helix by a second fixation tool;
pressing the second helix free end through the serosa; and
rotating the second fixation tool to rotate the second helix with respect to the lead body and the electrode head to advance the second helix substantially into the muscularis externa until the plate is drawn against the serosa.

42. The method of claim 30, wherein:

at least one of the first and second active fixation mechanisms comprises a hook comprising a hook shaft extending from a hook fixed end attached to the electrode head to a hook free end spaced from the plate of the electrode head terminating in a sharpened tip and barb; and the step of deploying the hook comprises
engaging the electrode head by a hook fixation tool; and
applying force through the hook fixation tool to press the hook free end through the serosa and lodge the hook substantially into the muscularis externa until the plate is drawn against the serosa.

43. The method of claim 42, wherein the stimulation/sense electrode is supported on the plate of the electrode head to bear against the serosa when the plate is drawn against the serosa.

44. The method of claim 42, wherein:

the hook is formed of a conductive electrode material; and
the hook fixed end is attached to a distal end of the lead conductor,
whereby the stimulation/sense electrode comprises at least a portion of the hook that is embedded substantially within the muscularis externa when the plate is drawn against the serosa.

45. The method of claim 42, wherein:

the hook is formed of a conductive electrode material;
a layer of insulation is formed over a first portion of the hook;
the hook fixed end is attached to a distal end of the lead conductor,
whereby the stimulation/sense electrode comprises at least an uninsulated second portion of the hook that is embedded substantially within the muscularis externa when the plate is drawn against the serosa.

46. The method of claim 42, wherein the plate is substantially planar and the hook shaft comprises a first portion extending from the hook fixed end at a first predetermined angle away from the plate and a second portion extending to the hook free end at a second predetermined angle.

47. The method of claim 42, wherein the plate is substantially planar and the hook shaft comprises a first portion and a second portion joined at a bend, the first portion extending from the hook fixed end to the bend at a first predetermined angle away from the plate and a second portion extending from the bend to the hook free end at a second predetermined angle selected to locate the hook free end further away from the plate than the bend.

48. The method of claim 42, wherein the plate is substantially planar and the hook shaft comprises a first portion and a second portion joined at a bend, the first portion extending from the hook fixed end to the bend at a first predetermined angle away from the plate and a second portion extending from the bend to the hook free end at a second predetermined angle selected to locate the hook free end closer to the plate than the bend.

49. The method of claim 42, wherein the plate is substantially planar and the hook shaft comprises a first portion extending from the hook fixed end at a first predetermined angle away from the plate and a second portion extending to the hook free end at a second predetermined angle.

50. The method of claim 42, wherein the electrode head is shaped to be engaged by the hook fixation tool that is manipulated to apply the insertion force to advance the hook free end through the serosa and into the muscularis externa.

51. The method of claim 42, wherein the hook free end is distanced from the plate enabling a depth of penetration from the plate in the range of 1 mm to 15 mm when the site comprises the antrum of the stomach wall or in the range of 1 mm to 10 mm when the site comprises corpus or fundus of the stomach wall to ensure that the helix free end does not extend substantially through the stomach wall.

52. The method of claim 30, wherein at least one electrode is supported on the plate of the electrode head to bear against the serosa when the plate is drawn against the serosa.

53. The method of claim 30, wherein:

at least one active fixation mechanism is formed of a conductive electrode material; and
the active fixation mechanism is electrically coupled to a distal end of the lead conductor,
whereby the stimulation/sense electrode comprises at least a portion of the active fixation mechanism that is embedded substantially within the muscularis externa when the plate is drawn against the serosa.

54. The method of claim 30, wherein:

at least one active fixation mechanism is formed of a conductive electrode material;
a layer of insulation is formed over a first portion of the active fixation mechanism;
the active fixation mechanism is electrically coupled to a distal end of the lead conductor,
whereby the stimulation/sense electrode comprises at least an uninsulated second portion of the active fixation mechanism that is embedded substantially within the muscularis externa when the plate is drawn against the serosa.

55. The method of claim 30, wherein the plurality of active fixation mechanisms each comprise a hook comprising a hook shaft extending from a hook fixed end attached to an electrode head to a hook free end spaced from the plate, a sharpened tip and barb formed at the hook free adapted to penetrate through the serosa and to advance into the muscularis externa when insertion force is applied to the electrode head until the plate is drawn against the serosa, whereupon advancement of the hook free end is halted and the barb engages the muscularis externa to inhibit retraction of the hook.

56. The method of claim 30, wherein an antiinflammatory material selected from the group consisting of steroids, anti-bacterial agents, baclofen, dexamethasone sodium phosphate or beclomethasone phosphate is incorporated into the electrode head or fixation mechanism.

57. The method of claim 30, wherein the plurality of lead body legs are permanently connected to the common lead body at the junction.

58. The method of claim 30, wherein the plurality of lead body legs are removably connected to the common lead body at the junction.

59. A system providing gastrointestinal sensing and/or stimulation comprising:
   a gastrointestinal lead comprising an elongated gastrointestinal lead body comprising a common lead body trunk extending from a connector assembly at a lead body proximal end comprising a plurality of connector elements of a lead connector assembly to a junction with a plurality of lead body legs that extend from the junction to a like plurality of lead body leg distal ends, an electrode head formed at each lead body leg distal end having a plate and supporting at least one stimulation/sense electrode and an active fixation mechanism, whereby a plurality of active fixation attachment mechanisms are supported by a plurality of electrode heads, and a plurality of lead conductors enclosed within the lead body, each lead conductor extending between a stimulation/sense electrode through a lead body leg and the lead body trunk to a proximal connector element of the connector assembly;
   first deploying means for deploying the first active fixation mechanism extending away from the plate of the electrode head and penetrating through the serosa and into the muscularis externa to draw the plate against the serosa and operatively contact the stimulation/sense electrode with the GI tract wall, whereby the plate inhibits further advancement of the active fixation mechanism and perforation of the GI tract wall and the active fixation mechanism inhibits dislodgement of the stimulation/sense electrode from operative contact with the GI tract wall;
   second deploying means for deploying the second active fixation mechanism extending away from the plate of the electrode head and penetrating through the serosa and into the muscularis externa to draw the plate against the serosa and operatively contact the stimulation/sense electrode with the GI tract wall, whereby the plate inhibits further advancement of the active fixation mechanism and perforation of the GI tract wall and the active fixation mechanism inhibits dislodgement of the stimulation/sense electrode from operative contact with the GI tract wall; and
   an implantable or external gastrointestinal stimulator having a gastrointestinal stimulator connector coupled with the lead connector assembly to conduct electrical stimulation from the implantable or external gastrointestinal stimulator between the first and second sites of the GI tract and to conduct electrical signals of the GI tract from the first and second sites to the implantable or external gastrointestinal stimulator.

60. The system of claim 59, wherein;
   the first active fixation mechanism comprises a helix comprising one or more coil turn extending from a helix fixed end and a helix free end and having a helix axis, the helix fixed end supported at the plate to extend the helix axis orthogonally to the plate; and
   the first deploying means comprises
      means for pressing the helix free end through the serosa; and
      means for rotating the helix to advance the helix into the muscularis externa until the plate is drawn against the serosa.

61. The system of claim 60, wherein the helix has an axial length enabling a depth of penetration from the plate in the range of 1 mm to 15 mm when the site comprises the antrum of the stomach wall or in the range of 1 mm to 10 mm when the site comprises corpus or fundus of the stomach wall to ensure that the helix free end does not extend substantially through the stomach wall.

62. The system of claim 60, wherein the stimulation/sense electrode is supported on the plate of the electrode head to bear against the serosa when the plate is drawn against the serosa.

63. The system of claim 60, wherein:
   the helix is formed of a conductive electrode material; and
   the helix fixed end is electrically coupled to a distal end of the lead conductor,
   whereby the stimulation/sense electrode comprises at least a portion of the helix that is embedded substantially within the muscularis externa when the plate is drawn against the serosa.

64. The system of claim 60, wherein:
   the helix is formed of a conductive electrode material;
   a layer of insulation is formed over a first portion of the helix;
   the helix fixed end is electrically coupled to a distal end of the lead conductor,
   whereby the stimulation/sense electrode comprises at least an uninsulated second portion of the helix that is embedded substantially within the muscularis externa when the plate is drawn against the serosa.

65. The system of claim 60, wherein the helix fixed end is fixedly attached to the plate, and the rotating means comprises a first fixation tool that engages the electrode head and is rotatable to rotate the lead body, the electrode head and the helix to advance the helix substantially into the muscularis externa until the plate is drawn against the serosa.

66. The system of claim 60, wherein the rotating means comprises a first fixation tool that engages the helix and rotates the helix with respect to the lead body and the electrode head to advance the helix substantially into the muscularis externa until the plate is drawn against the serosa.

67. The system of claim 60, wherein:
   the elongated lead body encloses a conductor lumen extending through the lead body trunk and the first lead body leg to the first electrode head located at the distal end of the first lead body leg supporting the helix;
   the lead conductor extends from a lead connector element through the conductor lumen and to the helix fixed end, whereby the lead connector element and lead conductor attached thereto are rotatable with respect to the lead connector assembly to rotate the helix attached thereto with respect to the plate to advance the helix free end through the serosa and substantially into the muscularis externa until the plate is drawn against the serosa.

68. The system of claim 60, wherein:

the first electrode head encloses a rotatable mechanism for supporting the helix fixed end;

the elongated lead body encloses a stylet lumen extending through the lead body trunk and the first lead body leg to the first electrode head located at the distal end of the first lead body leg supporting the helix; and the rotating means comprises a stylet having a stylet wire extendable through the stylet lumen to engage the rotatable mechanism to rotate the helix attached to the rotatable mechanism with respect to the plate to advance the helix free end through the serosa and substantially into the muscularis externa until the plate is drawn against the serosa.

69. The system of claim 60, wherein:

the second active fixation mechanism comprises a hook comprising a hook shaft extending from a hook fixed end attached to the second electrode head to a hook free end spaced from the plate of the second electrode head terminating in a sharpened tip and barb; and the second deploying means comprises a second fixation tool adapted to engage the second electrode head to apply force through the second fixation tool to press the hook free end through the serosa and lodge the hook substantially into the muscularis externa until the plate is drawn against the serosa.

70. The system of claim 59, wherein;

the first active fixation mechanism comprises a first helix comprising one or more coil turn extending from a first helix fixed end and a first helix free end and having a first helix axis, the first helix fixed end supported at and fixed to the plate to extend the first helix axis orthogonally to the plate;

the first deploying means comprises a first fixation tool for engaging the first electrode head, pressing the first helix free end through the serosa, and rotating the lead body, the electrode head, and the first helix to advance the first helix substantially into the muscularis externa until the plate is drawn against the serosa;

the second active fixation mechanism comprises a second helix comprising one or more coil turn extending from a second helix fixed end and a second helix free end and having a second helix axis, the second helix fixed end supported by a rotatable mechanism of the electrode head to extend the second helix axis orthogonally to the plate; and the second deploying means comprises a second fixation tool for engaging the second helix, pressing the second helix free end through the serosa, and rotating the second helix to advance the first helix substantially into the muscularis externa until the plate is drawn against the serosa.

71. The system of claim 59, wherein:

at least one of the first and second active fixation mechanisms comprises a hook comprising a hook shaft extending from a hook fixed end attached to the electrode head to a hook free end spaced from the plate of the electrode head terminating in a sharpened tip and barb; and the deploying means comprises a hook fixation tool adapted to engage the electrode head to apply force through the second fixation tool to press the hook free end through the serosa and lodge the hook substantially into the muscularis externa until the plate is drawn against the serosa the step of deploying the hook comprises engaging the electrode head by a hook fixation tool; and applying force through the hook fixation tool to press the hook free end through the serosa and lodge the hook substantially into the muscularis externa until the plate is drawn against the serosa.

72. The system of claim 71, wherein the stimulation/sense electrode is supported on the plate of the electrode head to bear against the serosa when the plate is drawn against the serosa.

73. The system of claim 71, wherein:

the hook is formed of a conductive electrode material; and the hook fixed end is attached to a distal end of the lead conductor, whereby the stimulation/sense electrode comprises at least a portion of the hook that is embedded substantially within the muscularis externa when the plate is drawn against the serosa.

74. The system of claim 71, wherein the plate is substantially planar and the hook shaft comprises a first portion extending from the hook fixed end at a first predetermined angle away from the plate and a second portion extending to the hook free end at a second predetermined angle.

75. The system of claim 71, wherein:

the hook is formed of a conductive electrode material;

a layer of insulation is formed over a first portion of the hook;

the hook fixed end is attached to a distal end of the lead conductor, whereby the stimulation/sense electrode comprises at least an uninsulated second portion of the hook that is embedded substantially within the muscularis externa when the plate is drawn against the serosa.

76. The system of claim 71, wherein the plate is substantially planar and the hook shaft comprises a first portion and a second portion joined at a bend, the first portion extending from the hook fixed end to the bend at a first predetermined angle away from the plate and a second portion extending from the bend to the hook free end at a second predetermined angle selected to locate the hook free end further away from the plate than the bend.

77. The system of claim 71, wherein the plate is substantially planar and the hook shaft comprises a first portion and a second portion joined at a bend, the first portion extending from the hook fixed end to the bend at a first predetermined angle away from the plate and a second portion extending from the bend to the hook free end at a second predetermined angle selected to locate the hook free end closer to the plate than the bend.

78. The system of claim 71, wherein the plate is substantially planar and the hook shaft comprises a first portion extending from the hook fixed end at a first predetermined angle away from the plate and a second portion extending to the hook free end at a second predetermined angle.

79. The system of claim 71, wherein the electrode head is shaped to be engaged by the hook fixation tool that is manipulated to apply the insertion force to advance the hook free end through the serosa and into the muscularis externa.

80. The system of claim 71, wherein the hook free end is distanced from the plate enabling a depth of penetration from the plate in the range of 1 mm to 15 mm when the site comprises the antrum of the stomach wall or in the range of 1 mm to 10 mm when the site comprises corpus or fundus of the stomach wall to ensure that the helix free end does not extend substantially through the stomach wall.

81. The system of claim 59, wherein at least one electrode is supported on the plate of the electrode head to bear against the serosa when the plate is drawn against the serosa.

82. The system of claim 59, wherein:
- at least one active fixation mechanism is formed of a conductive electrode material; and
- the active fixation mechanism is electrically coupled to a distal end of the lead conductor,
- whereby the stimulation/sense electrode comprises at least a portion of the active fixation mechanism that is embedded substantially within the muscularis externa when the plate is drawn against the serosa.

83. The system of claim 59, wherein:
- at least one active fixation mechanism is formed of a conductive electrode material;
- a layer of insulation is formed over a first portion of the active fixation mechanism;
- the active fixation mechanism is electrically coupled to a distal end of the lead conductor,
- whereby the stimulation/sense electrode comprises at least an uninsulated second portion of the active fixation mechanism that is embedded substantially within the muscularis externa when the plate is drawn against the serosa.

84. The system of claim 59, wherein the plurality of active fixation mechanisms each comprise a hook comprising a hook shaft extending from a hook fixed end attached to an electrode head to a hook free end spaced from the plate, a sharpened tip and barb formed at the hook free adapted to penetrate through the serosa and to advance into the muscularis externa when insertion force is applied to the electrode head until the plate is drawn against the serosa, whereupon advancement of the hook free end is halted and the barb engages the muscularis externa to inhibit retraction of the hook.

85. The system of claim 59, wherein an anti-inflammatory material selected from the group consisting of steroids, anti-bacterial agents, baclofen, dexamethasone sodium phosphate or beclomethasone phosphate is incorporated into the electrode head or fixation mechanism.

86. The system of claim 59, wherein the plurality of lead body legs are permanently connected to the common lead body at the junction.

87. The system of claim 59, wherein the plurality of lead body legs are removably connected to the common lead body at the junction.

* * * * *